US010329483B2

(12) United States Patent
Gray et al.

(10) Patent No.: US 10,329,483 B2
(45) Date of Patent: Jun. 25, 2019

(54) FLUORENE DERIVATIVES AS LIGHT EMITTING ELEMENTS FOR ELECTROLUMINESCENT DEVICES

(71) Applicant: Dow Global Technologies LLC, Midland, MI (US)

(72) Inventors: Kaitlyn Gray, Freeland, MI (US); Aaron Rachford, Midland, MI (US); David Laitar, Midland, MI (US); Sukrit Mukhopadhyay, Midland, MI (US); Robert Froese, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/540,336

(22) PCT Filed: Dec. 21, 2015

(86) PCT No.: PCT/US2015/066992
§ 371 (c)(1),
(2) Date: Jun. 28, 2017

(87) PCT Pub. No.: WO2016/109274
PCT Pub. Date: Jul. 7, 2016

(65) Prior Publication Data
US 2018/0002597 A1   Jan. 4, 2018

Related U.S. Application Data

(60) Provisional application No. 62/097,720, filed on Dec. 30, 2014.

(51) Int. Cl.
| | | |
|---|---|---|
| *C09K 11/06* | (2006.01) |
| *C07D 401/04* | (2006.01) |
| *C07D 251/24* | (2006.01) |
| *H01L 51/00* | (2006.01) |
| *C07D 409/04* | (2006.01) |
| *C07D 213/38* | (2006.01) |
| *C07F 9/6568* | (2006.01) |
| *H01L 51/50* | (2006.01) |

(52) U.S. Cl.
CPC ............ *C09K 11/06* (2013.01); *C07D 213/38* (2013.01); *C07D 251/24* (2013.01); *C07D 401/04* (2013.01); *C07D 409/04* (2013.01); *C07F 9/65685* (2013.01); *H01L 51/006* (2013.01); *H01L 51/0052* (2013.01); *H01L 51/0059* (2013.01); *H01L 51/0061* (2013.01); *H01L 51/0067* (2013.01); *H01L 51/0072* (2013.01); *C09K 2211/1007* (2013.01); *C09K 2211/1011* (2013.01); *C09K 2211/1014* (2013.01); *C09K 2211/1018* (2013.01); *C09K 2211/1029* (2013.01); *C09K 2211/1059* (2013.01); *C09K 2211/1092* (2013.01); *C09K 2211/1096* (2013.01); *H01L 51/5012* (2013.01)

(58) Field of Classification Search
CPC .. C07D 213/38; C07D 251/24; C07D 401/04; C07D 409/04; C07F 9/65685; H01L 51/0052; H01L 51/0059; H01L 51/006; H01L 51/0061; H01L 51/0067; H01L 51/0072
See application file for complete search history.

(56) References Cited

U.S. PATENT DOCUMENTS

| | | | |
|---|---|---|---|
| 8,361,638 B2 | 1/2013 | Stoessel et al. | |
| 8,384,068 B2 | 2/2013 | Kahle et al. | |
| 8,815,418 B2 | 8/2014 | Kim et al. | |
| 9,246,108 B2 * | 1/2016 | Ober | H01L 51/0071 |
| 9,966,537 B2 * | 5/2018 | Gray | C07D 403/12 |
| 9,972,792 B2 * | 5/2018 | De Vries | H01L 51/0079 |
| 2010/0019658 A1 | 1/2010 | Lin et al. | |
| 2010/0219406 A1 | 9/2010 | Kahle et al. | |
| 2011/0037027 A1 | 2/2011 | Stoessel et al. | |
| 2012/0049768 A1 | 3/2012 | Seo et al. | |
| 2012/0228554 A1 | 9/2012 | Franz et al. | |
| 2013/0248830 A1 * | 9/2013 | Welsh | H01L 51/0067 257/40 |
| 2014/0145149 A1 | 5/2014 | Lin et al. | |
| 2014/0183413 A1 * | 7/2014 | Ober | H01L 51/0071 252/500 |
| 2015/0141642 A1 | 5/2015 | Adachi et al. | |

FOREIGN PATENT DOCUMENTS

| | | | |
|---|---|---|---|
| CN | 103304540 A | * | 9/2013 |
| CN | 105399662 A | * | 3/2016 |
| WO | 03/017731 A1 | | 2/2003 |
| WO | 2011/037429 A2 | | 3/2011 |
| WO | 2011/053035 A2 | | 5/2011 |
| WO | 2013/154064 A1 | | 10/2013 |

OTHER PUBLICATIONS

X. Zhao et al., 34 Chinese Journal of Chemistry, 397-402 (2016) (Year: 2016).*

(Continued)

*Primary Examiner* — Alexander R Pagano
(74) *Attorney, Agent, or Firm* — Husch Blackwell LLP

(57) ABSTRACT

The present disclosure provides a composition comprising at least one compound selected from the group consisting of Compound 1, Compound 2, and combinations thereof, as shown below, and described herein: wherein, for Compound 1 and Compound 2, independently, $R_1$ and $R_2$ each independently is selected from the group consisting of hydrogen, a substituted alkyl, an unsubstituted alkyl, a substituted heteroalkyl, an unsubstituted heteroalkyl, a substituted aryl, an unsubstituted aryl, a substituted heteroaryl and an unsubstituted heteroaryl; wherein, for Compound 1 and Compound 2, independently, the Component A is selected from the group consisting of Group a) through Group h): wherein Group a) through Group h) are described herein.

15 Claims, 2 Drawing Sheets

(56) References Cited

OTHER PUBLICATIONS

Ino, M., et al., Journal of Membrane Science, 89, Mar. 30, 1994, pp. 101-109.
Simmons, D., The Journal of Histochemistry and Cytochemistry, vol. 38, 1990, pp. 41-49.
Tazuke, S., J. Org. Chem, 51, 1986, pp. 4548-4553.

* cited by examiner

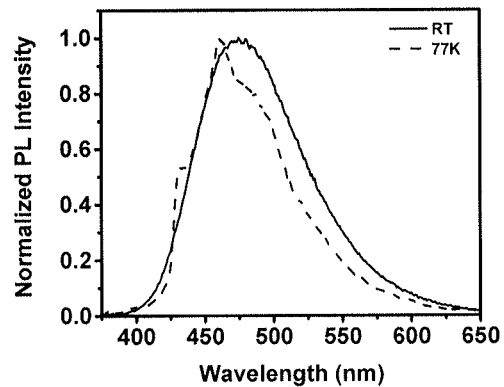
Figure 1. Photoluminescence Spectra of Example 1 in PMMA at room temperature and 77K upon 355 nm excitation.
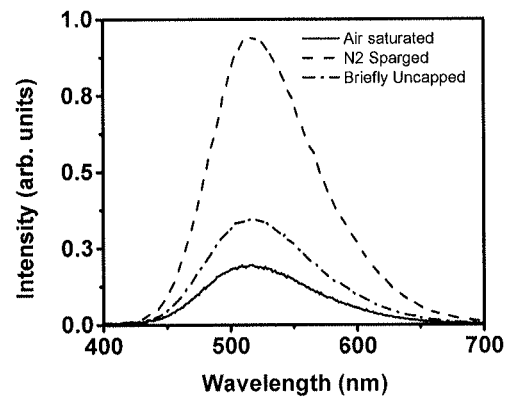
Figure 2. Photoluminescence of Example 1 dissolved in chloroform demonstrating sensitivity of the excited state to $O_2$. The wavelength of excitation is 355 nm.

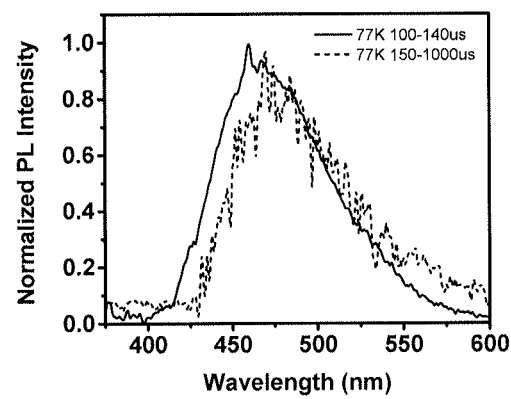
Figure 3. Time-resolved Emission Spectra (TRES) of Example 1 in PMMA at 77K. The wavelength of excitation is 355 nm. The intensities are normalized to highlight the shift to lower energy at longer delay times.

FLUORENE DERIVATIVES AS LIGHT EMITTING ELEMENTS FOR ELECTROLUMINESCENT DEVICES

REFERENCE TO RELATED APPLICATIONS

This application claims priority to U.S. provisional patent application No. 62/097,720 filed on 30 Dec. 2014, the entire content of which is incorporated by reference herein.

BACKGROUND

An OLED (organic light-emitting diode) is a light-emitting diode (LED), in which the emissive electroluminescent layer is a film of an organic compound, which emits light in response to an electric current. A typical OLED has a multi-layer structure, and typically includes an indium tin oxide (ITO) anode, and a metal cathode. Sandwiched between the ITO anode and the metal cathode are several organic layers, such as a hole injection layer (HIL), a hole transfer layer (HTL), an emitting material layer (EML), an electron transfer layer (ETL), and an electron injection layer (EIL).

Conventional OLED devices use emissive materials based on expensive iridium phosphorescent complexes or inefficient fluorescent based organic small molecules. The art recognizes the on-going need for new emissive materials that are more economical and/or more efficient than conventional iridium-based emissive materials or fluorescent-based emissive materials. The art recognizes the need for such emissive materials for organic thermally activated delayed fluorescence (TADF) emitters in particular.

SUMMARY

The present disclosure provides a composition that relates to a novel class of organic thermally activated delayed fluorescence (TADF) emitters.

The present disclosure provides a composition comprising at least one compound selected from the group consisting of Compound 1, Compound 2, and combinations thereof, as shown below:

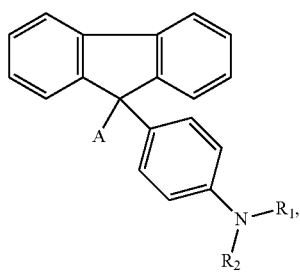
(Compound 1)

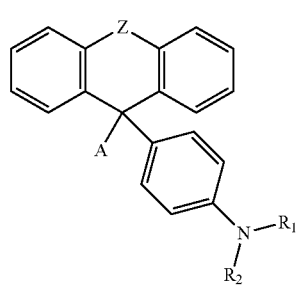
(Compound 2)

wherein, for Compound 1 and Compound 2, independently, $R_1$ and $R_2$ each independently is selected from the group consisting of hydrogen, a substituted alkyl, an unsubstituted alkyl, a substituted heteroalkyl, an unsubstituted heteroalkyl, a substituted aryl, an unsubstituted aryl, a substituted heteroaryl and an unsubstituted heteroaryl;

wherein, for Compound 1 and Compound 2, independently, the Component A is selected from the group consisting of Group a) through Group h):

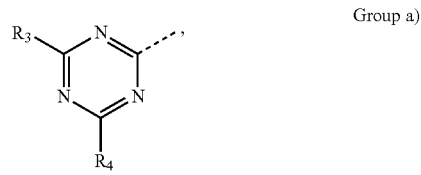
Group a)

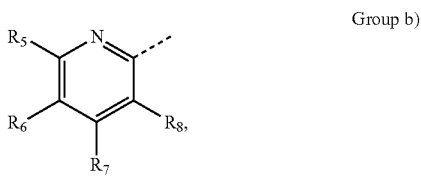
Group b)

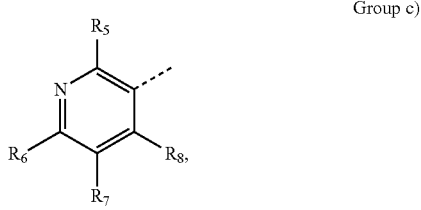
Group c)

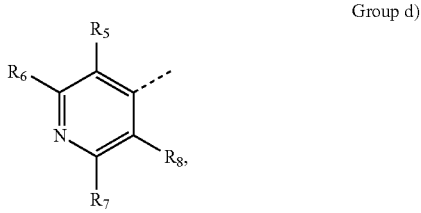
Group d)

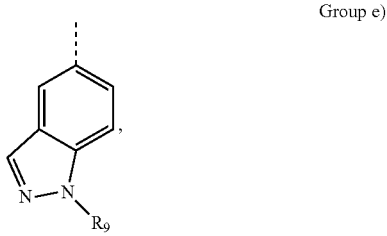
Group e)

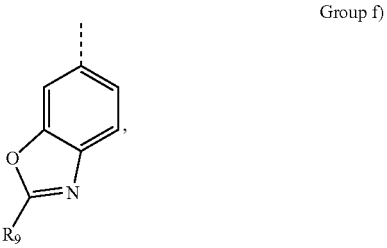
Group f)

-continued

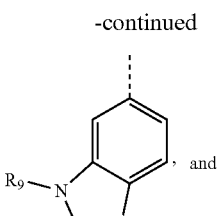
, and

Group g)

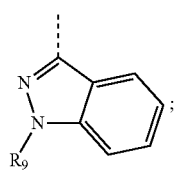
;

Group h)

and wherein for Group a), $R_3$ and $R_4$ each independently is selected from the group consisting of hydrogen, a substituted alkyl, an unsubstituted alkyl, a substituted aryl, an unsubstituted aryl, a substituted heteroaryl, and an unsubstituted heteroaryl;

wherein for Group b), $R_5$, $R_6$, $R_7$ and $R_8$ each independently is selected from the group consisting of hydrogen, a substituted alkyl, an unsubstituted alkyl, a substituted aryl, an unsubstituted aryl, a substituted heteroaryl, and an unsubstituted heteroaryl;

wherein for Group c), $R_5$, $R_6$, $R_7$ and $R_8$ each independently is selected from the group consisting of hydrogen, a substituted alkyl, an unsubstituted alkyl, a substituted aryl, an unsubstituted aryl, a substituted heteroaryl, and an unsubstituted heteroaryl;

wherein for Group d), $R_5$, $R_6$, $R_7$ and $R_8$ each independently is selected from the group consisting of hydrogen, a substituted alkyl, an unsubstituted alkyl, a substituted aryl, an unsubstituted aryl, a substituted heteroaryl, and an unsubstituted heteroaryl;

wherein for Group e), $R_9$ is selected from the group consisting of hydrogen, a substituted alkyl, an unsubstituted alkyl, a substituted aryl, an unsubstituted aryl, a substituted heteroaryl, and an unsubstituted heteroaryl;

wherein for Group f), $R_9$ is selected from the group consisting of hydrogen, a substituted alkyl, an unsubstituted alkyl, a substituted aryl, an unsubstituted aryl, a substituted heteroaryl, and an unsubstituted heteroaryl;

wherein for Group g), $R_9$ is selected from the group consisting of hydrogen, a substituted alkyl, an unsubstituted alkyl, a substituted aryl, an unsubstituted aryl, a substituted heteroaryl, and an unsubstituted heteroaryl;

wherein for Group h), $R_9$ is selected from the group consisting of hydrogen, a substituted alkyl, an unsubstituted alkyl, a substituted aryl, an unsubstituted aryl, a substituted heteroaryl, and an unsubstituted heteroaryl; and wherein, for Compound 2, Component Z is selected from the group consisting of $C(R_Z)_2$, $NR_Z$, $P(O)R_Z$, $PR_Z$, S, SO, $SO_2$, $Si(R_Z)_2$, and O;

wherein each $R_Z$ is, independently, selected from the group consisting of hydrogen, an unsubstituted alkyl, an unsubstituted aryl, and an alkoxy; and wherein, optionally, for Compound 1 and Compound 2, independently, one or more hydrogen atoms may be substituted with deuterium

BRIEF DESCRIPTION OF THE DRAWINGS

FIG. 1 is a photoluminescence spectrum for a composition in accordance with an embodiment of the present disclosure.

FIG. 2 is a photoluminescence spectrum for a composition in accordance with an embodiment of the present disclosure.

FIG. 3 is a time-resolved emission spectrum (TRES) for a compound in accordance with an embodiment of the present disclosure.

DETAILED DESCRIPTION

Definitions

Unless stated to the contrary, implicit from the context, or customary in the art, all parts and percents are based on weight. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The numerical ranges disclosed herein include all values from, and including, the lower value and the upper value. For ranges containing explicit values (e.g., 1 or 2, or 3 to 5, or 6, or 7) any subrange between any two explicit values is included (e.g., 1 to 2; 2 to 6; 5 to 7; 3 to 7; 5 to 6; etc.).

The term "alkoxy," as described herein, refers to an alkyl in which at least one hydrogen atom is substituted with an oxygen atom, O.

The term "alkyl," as described herein, refers to an organic radical derived from an aliphatic hydrocarbon by deleting one hydrogen atom therefrom. An alkyl group may be a linear, branched, cyclic or a combination thereof. The term "substituted alkyl," as used herein, refers to an alkyl, in which at least one hydrogen atom is substituted with a substituent that comprises at least one heteroatom. Heteroatoms include, but are not limited to, O, N, P and S. Substituents include, but are not limited to, halide, OR', $NR'_2$, $PR'_2$, $P(=O)R'_2$, $SiR'_3$; where each R' is independently a $C_1$-$C_{20}$ hydrocarbyl group.

The term "aryl," as described herein, refers to an organic radical derived from aromatic hydrocarbon by deleting one hydrogen atom therefrom. An aryl group may be a monocyclic and/or fused ring system, each ring of which suitably contains from 5 to 7, preferably from 5 or 6 atoms. Structures wherein two or more aryl groups are combined through single bond(s) are also included. Specific examples include, but are not limited to, phenyl, tolyl, naphthyl, biphenyl, anthryl, indenyl, fluorenyl, benzofluorenyl, phenanthryl, triphenylenyl, pyrenyl, perylenyl, chrysenyl, naphtacenyl, fluoranthenyl and the like. The naphthyl may be 1-naphthyl or 2-naphthyl, the anthryl may be 1-anthryl, 2-anthryl or 9-anthryl, and the fluorenyl may be any one of 1-fluorenyl, 2-fluorenyl, 3-fluorenyl, 4-fluorenyl and 9-fluorenyl. The term "substituted aryl," as used herein, refers to an aryl, in which at least one hydrogen atom is substituted with a substituent comprising at least one heteroatom. Heteroatoms include, but are not limited to, O, N, P and S. Substituents include, but are not limited to, halide OR', $NR'_2$, $PR'_2$, $P(=O)R'_2$, $SiR'_3$; where each R' is independently a $C_1$-$C_{20}$ hydrocarbyl group.

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

"Dopant" and like terms, refer to a material that undergoes radiative emission from an excited state. This excited state can be generated by application of electrical current in an electroluminescent device and is either singlet or triplet in character. The term "fluorescent emission," as used herein, refers to radiative emission from a singlet excited state. The term "phosphorescent emission," as used herein, refers to radiative emission from a triplet excited state. For a dopant that undergoes primarily fluorescent emission, the term "triplet harvesting," as used herein, refers to the ability to also harvest triplet excitons. The term "thermally activated delayed fluorescence (TADF)," as used herein, refers to fluorescent emission utilizing triplet harvesting, enabled by a thermally accessible singlet excited state.

"Electron Volt" or "eV" is the amount of energy gained (or lost) by the charge of a single electron moved across an electric potential difference of one volt.

"Emitting layer" and like terms, refer to a layer which is composed of a dopant and one or more host materials.

The term "heteroalkyl," as described herein, refers to an alkyl group, in which at least one carbon atom or CH group or $CH_2$ is substituted with a heteroatom or a chemical group containing at least one heteroatom. Heteroatoms include, but are not limited to, O, N, P and S. A heteroalkyl group may be a linear, branched, cyclic or a combination thereof. The term "substituted heteroalkyl," as used herein, refers to an heteroalkyl, in which at least one hydrogen atom is substituted with a substituent that comprises at least one heteroatom. Heteroatoms include, but are not limited to, O, N, P and S. Substituents include, but are not limited to, halide, OR', $NR'_2$, $PR'_2$, $P(=O)R'_2$, $SiR'_3$; where each R' is independently a $C_1$-$C_{20}$ hydrocarbyl group.

The term "heteroaryl," as described herein, refers to an aryl group, in which at least one carbon atom or CH group or $CH_2$ is substituted with a heteroatom or a chemical group containing at least one heteroatom. Heteroatoms include, but are not limited to, O, N, P and S. The heteroaryl may be a 5- or 6-membered monocyclic heteroaryl or a polycyclic heteroaryl which is fused with one or more benzene ring(s), and may be partially saturated. The structures having one or more heteroaryl group(s) bonded through a single bond are also included. The heteroaryl groups may include divalent aryl groups of which the heteroatoms are oxidized or quarternized to form N-oxides, quaternary salts, or the like. Specific examples include, but are not limited to, monocyclic heteroaryl groups, such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl; polycyclic heteroaryl groups, such as benzofuranyl, fluoreno[4,3-b]benzofuranyl, benzothiophenyl, fluoreno[4,3-b]benzothiophenyl, isobenzofuranyl, benzimidazolyl, benzothiazolyl, benzisothiazolyl, benzisoxazolyl, benzoxazolyl, isoindolyl, indolyl, indazolyl, benzothia-diazolyl, quinolyl, isoquinolyl, cinnolinyl, quinazolinyl, quinoxalinyl, carbazolyl, phenanthridinyl and benzodioxolyl; and corresponding N-oxides (for example, pyridyl N-oxide, quinolyl N-oxide) and quaternary salts thereof. The term "substituted heteroaryl," as used herein, refers to a heteroaryl in which at least one hydrogen atom is substituted with a substituent comprising at least one heteroatom. Heteroatoms include, but are not limited to, O, N, P and S. Substituents include, but are not limited to, halide OR', $NR'_2$, $PR'_2$, $P(=O)R'_2$, $SiR'_3$; where each R' is independently a $C_1$-$C_{20}$ hydrocarbyl group.

"Hole transport layer (HTL)," and like terms, refers to a layer made from a material, which transports holes. High hole mobility is recommended for OLED devices. The HTL is used to help block passage of electrons transported by the emitting layer. Small electron affinity is typically required to block electrons. The HTL should desirably have larger triplets to block exciton migrations from an adjacent EML layer. Examples of HTL compounds include, but are not limited to, di(p-tolyl)aminophenyl]cyclohexane (TPAC), N,N-diphenyl-N,N-bis(3-methylphenyl)-1,1-biphenyl-4,4-diamine (TPD), and N,N'-diphenyl-N,N bis(1-naphthyl)-(1,1'-biphenyl)-4,4'-diamine (NPB).

"Host" and like terms refer to a material that is doped with a dopant. The opto-electrical properties of the host material may differ based on which type of dopant (Phosphorescent or Fluorescent) is used. For Fluorescent dopants, the assisting host materials should have good spectral overlap between adsorption of the dopant and emission of the host to induce good Forster transfer to dopants. For Phosphorescent dopants and TADF dopants, the assisting host materials should have high triplet energies to confine triplets on the dopant.

The term "hydrocarbon," as used herein, refers to a chemical group containing only hydrogen and carbon atoms. The term "substituted hydrocarbon," as used herein, refers to a hydrocarbon in which at least one hydrogen atom is substituted with a substituent comprising at least one heteroatom. Heteroatoms include, but are not limited to, a halide, O, N, P and S. Substituents include, but are not limited to, halide, OR', $NR'_2$, $PR'_2$, $P(=O)R'_2$, $SiR'_3$; where each R' is independently a $C_1$-$C_{20}$ hydrocarbyl group.

The term "independently," or "each is independently selected from," or like terms refers to the separate selection of an element for each individual member within a target group. For example, the term "for each of Compound 1 through Compound 5, independently, $R_1$ through $R_5$ each independently is selected from methyl, ethyl, and propyl" means (i) the property of a given substituent $R_1$-$R_5$ with respect to each Compound 1-5 is separate and individual (i.e., $R_1$ (methyl) of Compound 1 can be the same or different element as $R_1$ (methyl, ethyl, or propyl) for Compounds 2, 3, 4, or 5) and (ii) the selection for substituents $R_1$ through $R_5$ is separate for each individual substituent (i.e., $R_1$ (ethyl) can be the same or different element with respect to $R_2$, $R_3$, $R_4$, and $R_5$ (methyl, ethyl, or propyl).

The S1-T1 gap is defined as the energy difference between the lowest energy singlet excited state and lowest energy triplet excited state.

1. Composition

The present disclosure provides a composition. The composition includes at least one compound selected from Compound 1, Compound 2, and a combination of Compound 1 and Compound 2.

The structures for Compound 1 and Compound 2 are provided below.

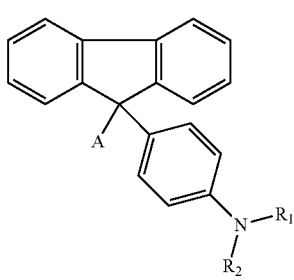

(Compound 1)

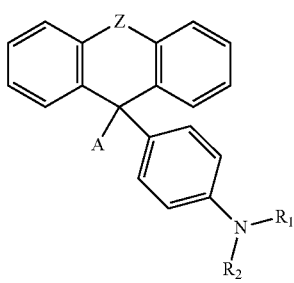

(Compound 2)

For Compound 1 and Compound 2, independently, $R_1$ and $R_2$ each independently is selected from hydrogen, a substituted alkyl, an unsubstituted alkyl, a substituted heteroalkyl, an unsubstituted heteroalkyl, a substituted aryl, an unsubstituted aryl, a substituted heteroaryl and an unsubstituted heteroaryl.

For Compound 1 and Compound 2, independently, the Component A is selected from the Group a) through Group h). The structure for each of Group a) through Group h) is provided below.

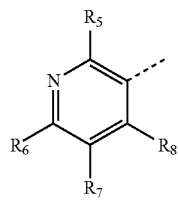

Group a)

For Group a), $R_3$ and $R_4$ each independently is selected from hydrogen, a substituted alkyl, an unsubstituted alkyl, a substituted aryl, an unsubstituted aryl, a substituted heteroaryl, an unsubstituted heteroaryl.

Group b)

For Group b), $R_5$, $R_6$, $R_7$ and $R_8$ each independently is selected from hydrogen, a substituted alkyl, an unsubstituted alkyl, a substituted aryl, an unsubstituted aryl, a substituted heteroaryl, and an unsubstituted heteroaryl.

Group c)

For Group c), $R_5$, $R_6$, $R_7$ and $R_8$ each independently is selected from hydrogen, a substituted alkyl, an unsubstituted alkyl, a substituted aryl, an unsubstituted aryl, a substituted heteroaryl, and an unsubstituted heteroaryl.

Group d)

For Group d), $R_5$, $R_6$, $R_7$ and $R_8$ each independently is selected from hydrogen, a substituted alkyl, an unsubstituted alkyl, a substituted aryl, an unsubstituted aryl, a substituted heteroaryl, and an unsubstituted heteroaryl.

Group e)

For Group e), $R_9$ is selected from hydrogen, a substituted alkyl, an unsubstituted alkyl, a substituted aryl, an unsubstituted aryl, a substituted heteroaryl, and an unsubstituted heteroaryl.

Group f)

For Group f), $R_9$ is selected from hydrogen, a substituted alkyl, an unsubstituted alkyl, a substituted aryl, an unsubstituted aryl, a substituted heteroaryl, and an unsubstituted heteroaryl.

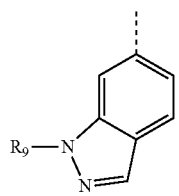

Group g)

For Group g), $R_9$ is selected from hydrogen, a substituted alkyl, an unsubstituted alkyl, a substituted aryl, an unsubstituted aryl, a substituted heteroaryl, and an unsubstituted heteroaryl.

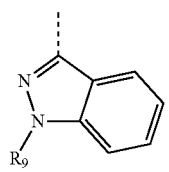

Group h)

For Group h), $R_9$ is selected from hydrogen, a substituted alkyl, an unsubstituted alkyl, a substituted aryl, an unsubstituted aryl, a substituted heteroaryl, and an unsubstituted heteroaryl.

For Compound 2, Component Z is selected from $CR_{(Z)2}$, $NR_Z$, $P(O)R_Z$, $PR_Z$, S, SO, $SO_2$, $SiR_{(Z)2}$, and O. $R_Z$ is selected from hydrogen, an unsubstituted alkyl, an unsubstituted aryl, and an alkoxy.

In an embodiment, each of Compound 1 and Compound 2, independently, has a purity greater than 99 percent (%) as determined by analytical methods, for example, high-performance liquid chromatography (HPLC), liquid chromatography (LC), and/or liquid chromatography-mass spectrometry (LC-MS or HPLC-MS).

In an embodiment, each of Compound 1 and Compound 2, independently, has a highest occupied molecular orbital (HOMO) level from −4.5 electron volts (eV), or −4.75 eV, or −5.0 eV, or −5.25 eV to −5.50 eV, or −5.75 eV, or −6.0 eV.

In an embodiment, each of Compound 1 and Compound 2, independently, has a lowest unoccupied molecular orbital (LUMO) level from −1.2 eV, or −1.3 eV, or −1.4 eV, or −1.5 eV to −1.6 eV, or −1.8 eV, or −2.0 eV, or −2.2 eV.

In an embodiment, each of Compound 1 and Compound 2, independently, has a Triplet energy level (T1) from 2.5 eV, or 2.6 eV, or 2.7 eV to 2.8 eV, or 2.9 eV, or 3.0 eV, or 3.1 eV, or 3.2 eV.

In an embodiment, each of Compound 1 and Compound 2, independently, has an S1-T1 gap from 0.01 eV, or 0.05 eV, or 0.1 eV, or 0.20 eV, or 0.25 eV, to 0.29 eV, 0.30 eV, or 0.34 eV, or 0.35 eV, or 0.39 eV or 0.4 eV.

A. Compound 1

In an embodiment, the composition includes Compound 1 as shown below.

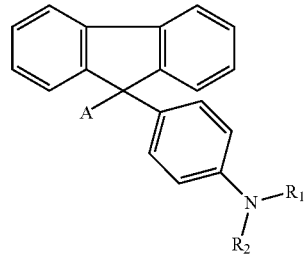

Compound 1

For Compound 1, $R_1$ and $R_2$ each independently is selected from a substituted aryl, an unsubstituted aryl, a substituted heteroaryl, and an unsubstituted heteroaryl.

In an embodiment, the composition includes Compound 1. $R_1$ and $R_2$ for Compound 1 each independently is selected from an unsubstituted aryl and an unsubstituted heteroaryl.

In an embodiment, the composition includes Compound 1. Component A for Compound 1 is Group a) below.

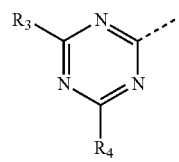

Group a)

For Group a), $R_3$ and $R_4$ each independently is selected from hydrogen, an unsubstituted aryl, or an unsubstituted heteroaryl.

In an embodiment, the composition includes Compound 1 with Group a). Compound 1 with Group a) has the Structure (i) below.

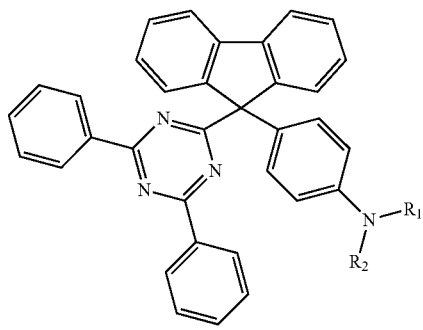

Structure (i)

$R_1$ and $R_2$ for Structure (i) each independently is selected from an unsubstituted aryl and an unsubstituted heteroaryl.

In an embodiment, the composition includes Compound 1 with Group a). Compound 1 with Group a) has the Structure (ii) below:

Structure (ii)

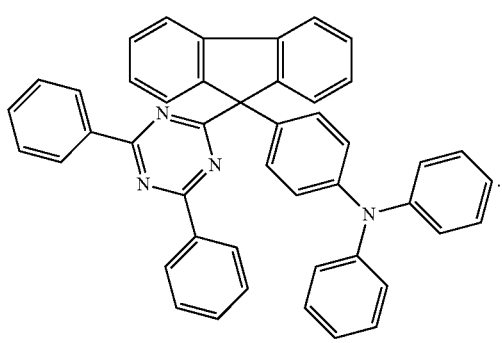

In an embodiment, the composition includes Compound 1 with Group a). Compound 1 has the Structure (iii) as shown below.

Structure (iii)

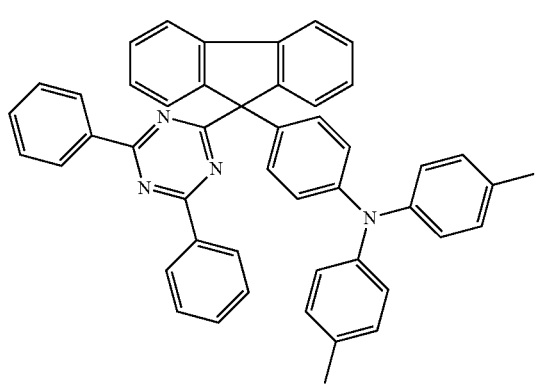

In an embodiment, the composition includes Compound 1 with Group a). Compound 1 has the Structure (iv) as shown below.

Structure (iv)

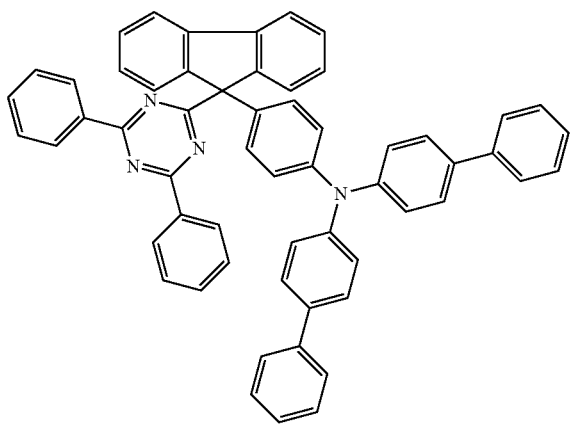

In an embodiment, the composition includes Compound 1 with Group a). Compound 1 has the Structure (v) as shown below.

Structure (v)

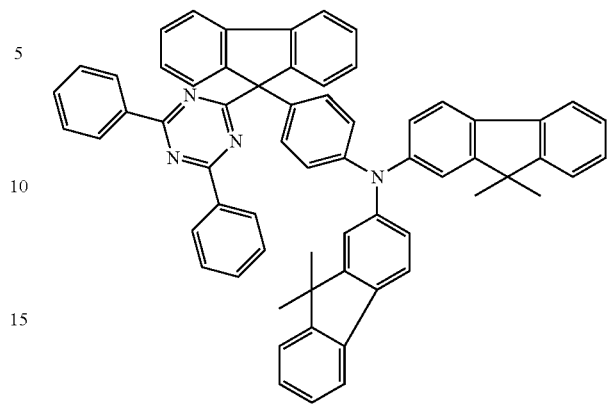

In an embodiment, the composition includes Compound 1. Component A for Compound 1 is Group b).

Group b)

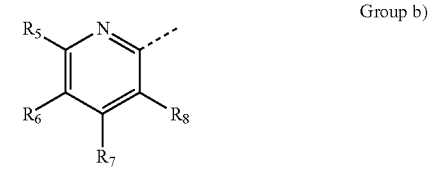

For Group b), $R_5$, $R_6$, $R_7$ and $R_8$ each independently is selected from hydrogen, a substituted aryl, an unsubstituted aryl, a substituted heteroaryl, and an unsubstituted heteroaryl.

In an embodiment, the composition includes Compound 1 with Group b). Compound 1 with Group b) has the Structure (vi) below.

Structure (vi)

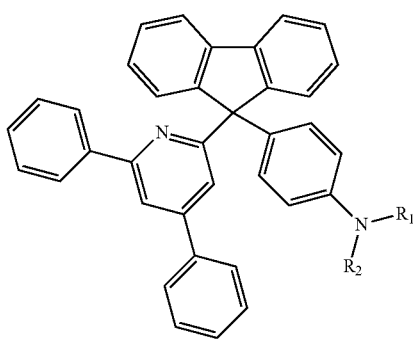

$R_1$ and $R_2$ for Structure (vi) each independently is selected from an unsubstituted aryl and an unsubstituted heteroaryl.

In an embodiment, the composition includes Compound 1 with Group b). Compound 1 with Group b) has the Structure (vii) below.

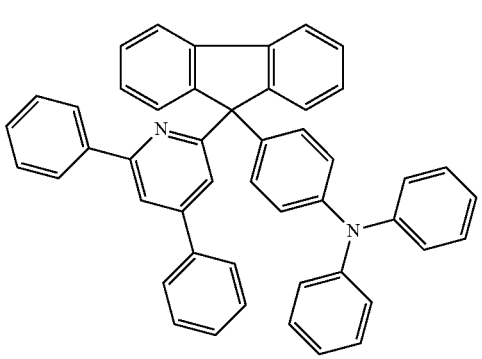

Structure (vii)

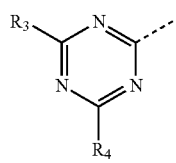

Group a)

For Group a), $R_3$ and $R_4$ each independently is hydrogen, an unsubstituted aryl, or an unsubstituted heteroaryl.

In an embodiment, the composition includes Compound 2 with Group a). Compound 2 with Group a) has the Structure (viii) below.

In an embodiment, the composition includes Compound 1. Compound 1 may have any of Structure (i) through Structure (vii) as previously disclosed. Compound 1 has a S1-T1 gap from 0.01 eV, or 0.05 eV, or 0.1 eV, or 0.20 eV, or 0.25 eV, to 0.29 eV, 0.30 eV, or 0.34 eV, or 0.35 eV, or 0.39 eV, or 0.4 eV.

In an embodiment, the composition includes Compound 1. Compound 1 may have any of Structure (i) through Structure (vii) as previously disclosed. Compound 1 has a Triplet energy level from 1.7 eV, or 1.9 eV, or 2.0 eV or, 2.5 eV to 2.7 eV, or 2.9 eV, or 3.0 eV, or 3.1 eV, or 3.2 eV.

Compound 1 may comprise two or more embodiments disclosed herein.

B. Compound 2

In an embodiment, the composition includes Compound 2 as shown below.

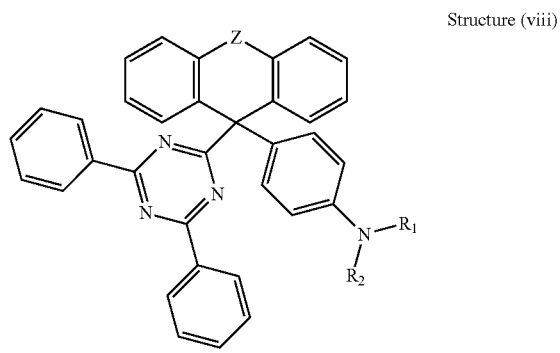

Structure (viii)

For Structure (viii) $R_1$ and $R_2$ each independently is selected from a substituted aryl, an unsubstituted aryl, a substituted heteroaryl, and an unsubstituted heteroaryl. For Structure (viii), Component Z is selected from $CR_{(Z)2}$, $NR_Z$, $P(O)R_Z$, $PR_Z$, S, SO, $SO_2$, $SiR_{(Z)2}$, and O. $R_Z$ is selected from hydrogen, unsubstituted alkyl, unsubstituted aryl, and an alkoxy.

In an embodiment, the composition includes Compound 2 with Group a) and Component Z is $NR_Z$. Compound 2 Group a) has the Structure (ix) as shown below.

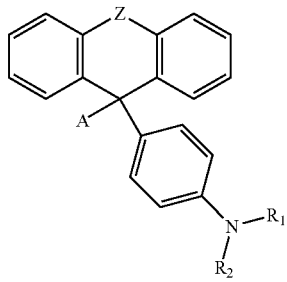

Compound 2

For Compound 2, $R_1$ and $R_2$ each independently is selected from substituted aryl, unsubstituted aryl, a substituted heteroaryl, and an unsubstituted heteroaryl.

For Compound 2, Component A is selected from Group a) through Group h) as described above.

For Compound 2, Component Z is selected from $CR_{(Z)2}$, $NR_Z$, $P(O)R_Z$, $PR_Z$, S, SO, $SO_2$, $SiR_{(Z)2}$, and O. For the Component Z, Rz is selected from an unsubstituted alkyl, an unsubstituted aryl, and an alkoxy.

In an embodiment, the composition includes Compound 2. For Compound 2, $R_1$ and $R_2$ each independently is selected from unsubstituted aryl and unsubstituted heteroaryl.

In an embodiment, the composition includes Compound 2. Component A for Compound 2 is Group a) as shown below.

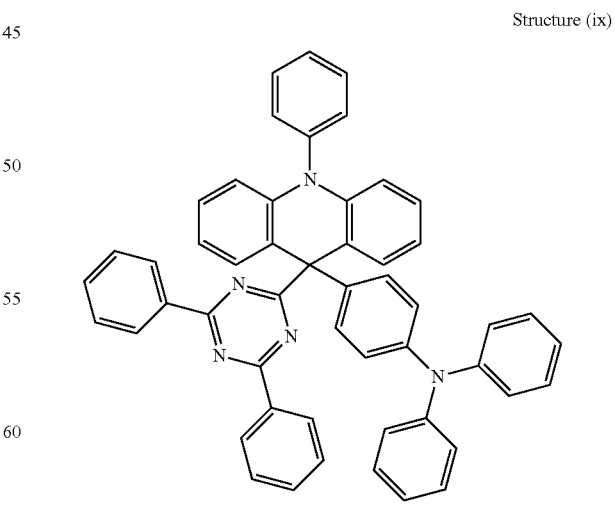

Structure (ix)

In an embodiment, the composition includes Compound 2 with Group a) and Component Z is $P(O)R_Z$. Compound 2 has the Structure (x) as shown below.

Structure (x)

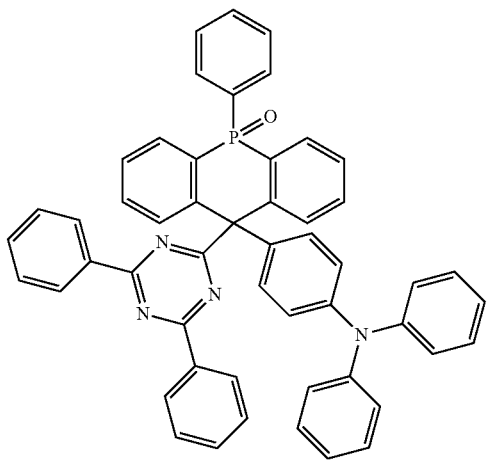

In an embodiment, the composition includes Compound 2 with Group a) and Component Z is $CR_{(Z)2}$. Compound 2 has the Structure (xi) as shown below.

Structure (xi)

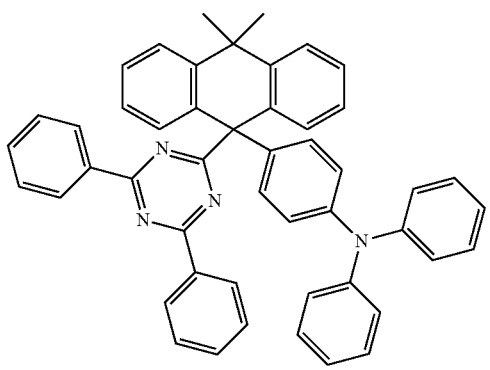

In an embodiment, the composition includes Compound 2 with Group a) and Component Z is sulfur, S. Compound 2 has the Structure (xii) as shown below.

Structure (xii)

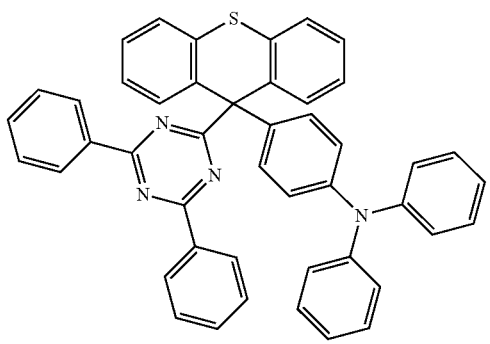

In an embodiment, the composition includes Compound 2 with Group a) and Component Z is $SO_2$. Compound 2 has the Structure (xiii) as shown below.

Structure (xiii)

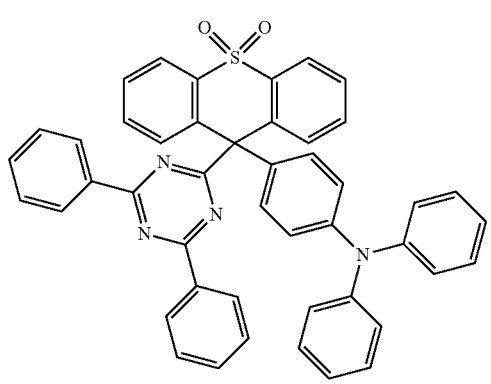

In an embodiment, the composition includes Compound 2. Component A for Compound 2 is Group b) shown below.

Group b)

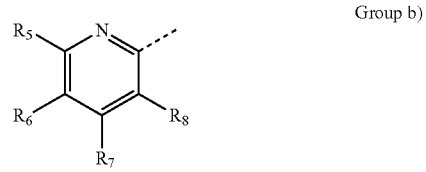

For Group b), $R_5$, $R_6$, $R_7$ and $R_8$ each independently is selected from hydrogen, a substituted aryl, an unsubstituted aryl, a substituted heteroaryl, and an unsubstituted heteroaryl.

In an embodiment, the composition includes Compound 2. Compound 2 has the Structure (xiv) as shown below.

Structure (xiv)

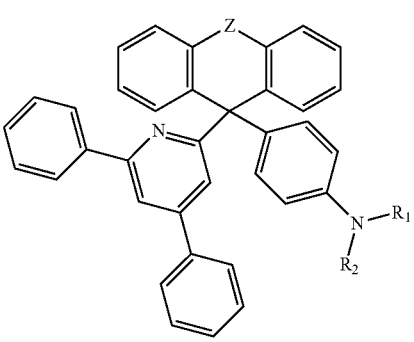

For Structure (xiv), $R_1$ and $R_2$ each independently is selected from an unsubstituted aryl and an unsubstituted heteroaryl.

For Structure (xiv), Component Z is selected from $CR_{(Z)2}$, $NR_Z$, $P(O)R_Z$, $PR_Z$, S, SO, $SO_2$, $SiR_{(Z)2}$, and O. $R_Z$ for Component Z is selected from hydrogen, unsubstituted alkyl, unsubstituted aryl, and alkoxy.

In an embodiment, the composition includes Compound 2 with Group b) and Component Z is $NR_Z$. Compound 2 has the Structure (xv) as shown below.

Structure (xv)

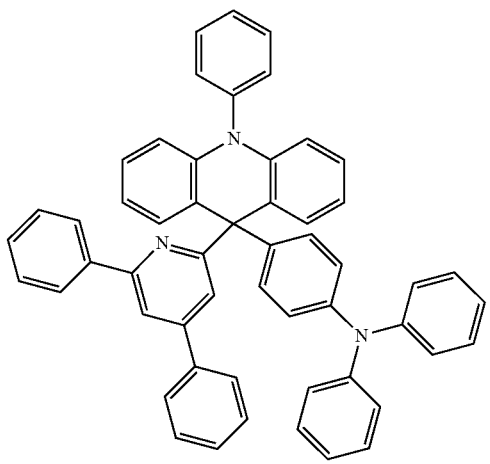

In an embodiment, the composition includes Compound 2 with Group b) and Component Z is SO$_2$. Compound 2 has the Structure (xvi) as shown below.

Structure (xvi)

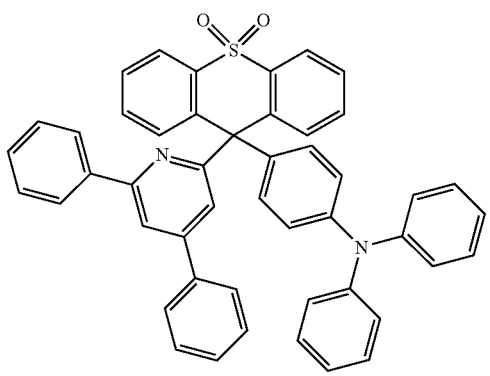

In an embodiment, the composition includes Compound 2 with Group b) and Component Z is P(O)R$_Z$. Compound 2 has the Structure (xvii) as shown below.

Structure (xvii)

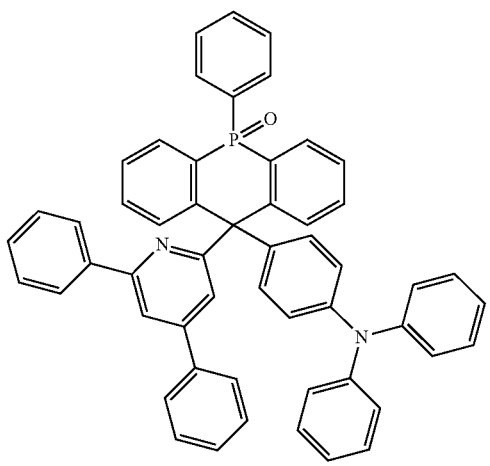

In an embodiment, the composition includes Compound 2 with Group b) and Component Z is SO$_2$. Compound 2 has the Structure (xviii) as shown below.

Structure (xviii)

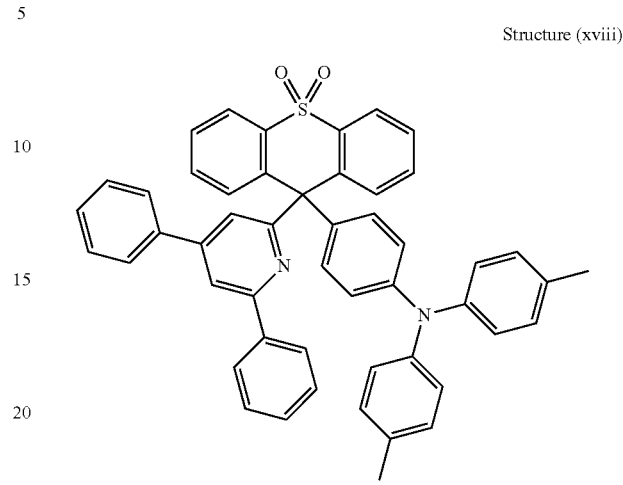

In an embodiment, the composition includes Compound 2 with Group b) and Component Z is SO$_2$. Compound 2 has the Structure (xix) as shown below.

Structure (xix)

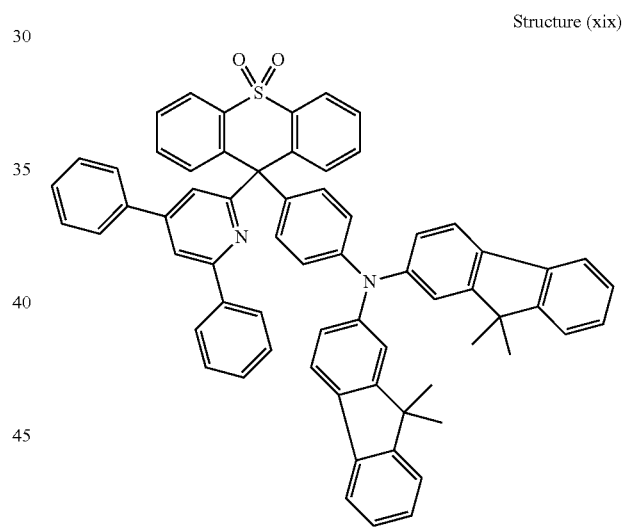

In an embodiment, the composition includes Compound 2. Compound 2 may have any of Structure (viii) through Structure (xix) as previously disclosed. Compound 2 has a S1-T1 gap from 0.01 eV, or 0.05 eV, or 0.1 eV, or 0.20 eV, or 0.25 eV, to 0.29 eV, 0.30 eV, or 0.34 eV, or 0.35 eV, or 0.39 eV or 0.4 eV.

In an embodiment, the composition includes Compound 2. Compound 2 may have any of Structure (viii) through Structure (xix) as previously disclosed. Compound 2 has a Triplet energy level from 1.7 eV, or 1.9 eV, or 2.0 eV or, 2.5 eV to 2.7 eV, or 2.9 eV, or 3.0 eV, or 3.1 eV, or 3.2 eV.

Compound 2 may comprise two or more embodiments disclosed herein.

2. Film

The present disclosure provides a film. The film includes, or is otherwise formed from, the present composition.

In an embodiment, the film includes the composition composed of Compound 1, Compound 2, or a combination of Compound 1 and Compound 2. Compound 1 and Compound 2 can have any structure previously disclosed herein.

In an embodiment, the film includes the composition composed of Compound 1, Compound 2, or a combination of Compound 1 and Compound 2. Each of Compound 1 and Compound, individually, includes Component A selected from Group a), Group b), Group c), Group d), Group e), and Group f), Group g), and Group h). Compound 2 includes Component Z selected from $C(R_Z)_2$, $NR_Z$, $P(O)R_Z$, $PR_Z$, S, SO, $SO_2$, $Si(R_Z)_2$, and O.

In an embodiment, the film includes the composition composed of two or more compounds. The two or more compounds may be (i) any two or more Compound 1s with different Group a) through Group h), (ii) any two or more Compound 2s with different Group a) through Group h) alone, or in combination with two or more different Z Components, and (iii) any combination of (i) and (ii).

In an embodiment, the film formed from the present composition emits light by TADF.

In an embodiment, the film is formed with an evaporative process.

In an embodiment, the film is formed in a solution process.

The present film may comprise two or more embodiments disclosed herein.

3. Device

The present disclosure provides an electronic device. The electronic device includes at least one component that includes, or is otherwise formed from, the present composition.

In an embodiment, the electronic device includes a film or a film layer. The film or film layer includes any film as previously disclosed herein.

In an embodiment, the electronic device has a component that includes the composition composed of Compound 1, Compound 2, or a combination of Compound 1 and Compound 2. Compound 1 and Compound 2 can have any structure previously disclosed herein.

In an embodiment, the electronic device has a component that includes the composition composed of Compound 1, Compound 2, or a combination of Compound 1 and Compound 2. Each of Compound 1 and Compound 2, individually, includes Component A selected from Group a), Group b), Group c), Group d), Group e), and Group f), Group g), and Group h). Compound 2 includes Component Z selected from $C(R_Z)_2$, $NR_Z$, $P(O)R_Z$, $PR_Z$, S, SO, $SO_2$, $Si(R_Z)_2$, and O.

In an embodiment, the electronic device has a component that includes the composition composed of two or more compounds. The two or more compounds may be (i) any two or more Compound 1s with different Group a) through Group h), (ii) any two or more Compound 2s with different Group a) through Group h) alone, or in combination with two or more different Z Components, and (iii) any combination of (i) and (ii).

In an embodiment, the electronic device is an organic light-emitting diode (OLED) device. The present composition can be present in one, some, or all of the following layers: hole injection layer (HIL), a hole transport layer (HTL), an emitting material layer (EML), an electron transport layer (ETL), and an electron injection layer (EIL). As a layer, the present composition has a layer thickness from 5 nanometers (nm), or 10 nm, or 20 nm, or 25 nm to 30 nm, or 35 nm, or 40 nm, or 50 nm, or 60 nm, or 70 nm, or 80 nm, or 90 nm.

In an embodiment, the present composition is a host material in an OLED device.

In an embodiment, the electronic device is an OLED device wherein visible light is emitted upon application of an electrical current across the OLED device.

In an embodiment, the electronic device is an OLED device and the present composition is a dopant in the emitting layer. When the present composition is the dopant, the host material has a triplet energy level higher than that of the doped emitter molecule. When the present composition is the dopant, a nonlimiting example of a suitable host material is (oxybis(2,1-phenylene))bis(diphenylphosphine oxide) (DPEPO). Additional host materials can be found in Yook et al. "Organic Materials for Deep Blue Phosphorescent Organic Light-Emitting Diodes" Adv. Mater. 2012, 24, 3169-3190, and in Mi et al. "Molecular Hosts for Triplet Emitters in Organic Light-Emitting Diodes and the Corresponding Working Principle" Sci. China Chem. 2010, 53, 1679.

In an embodiment, the present composition is in the emitting layer of the OLED device and is present in an amount from 1.0 wt %, or 5 wt %, or 15 wt % to 25 wt %, or 30 wt %, or 40 wt % based on the total weight of the emitting layer.

In an embodiment, the OLED device contains the present composition in the emitting layer and the OLED device emits light by way of TADF. In a further embodiment, the TADF-emitted light is visible light.

The present electronic device may comprise a combination of two or more embodiments disclosed herein.

Some embodiments of the present disclosure will now be described in detail in the following Examples.

EXAMPLES

1. Reagents and Test Methods

All solvents and reagents are obtained from commercial vendors, including Sigma-Aldrich, CombiBlocks, and AK Scientific, and are used in the highest available purities, and/or when necessary, recrystallized before use. Dry solvents are purchased from Sigma-Aldrich. All experiments involving "water sensitive compounds" are conducted in "oven dried" glassware, under nitrogen atmosphere, or in a glovebox. Reactions are monitored by high-performance liquid chromatography (HPLC) on an Agilent 1260 Infinity HPLC equipped with a Zorbax SB-C8 (4.6×150 mm, 3.5 micron) column. Flash chromatography is performed on an ISCO COMBIFLASH system with GRACERESOLV cartridges.

$^1$H-NMR-spectra are obtained on a Bruker 400 MHz Spectrometer equipped with a B-ACS 60 sample changer and a 5 mm PABBO broadband probe with Z-gradients unless otherwise noted. The chemical shifts are referenced to TMS ($\delta$=0.00) in CDCl$_3$.

$^{13}$C-NMR spectra (100 MHz) are obtained on a Bruker 400 MHz Spectrometer equipped with a B-ACS 60 sample changer and a 5 mm PABBO broadband probe with Z-gradients, and referenced to TMS ($\delta$=0.00) in CDCl$_3$.

Routine LC/MS studies are carried out as follows. Five microliter aliquots of the sample, as "3 mg/ml solution in THF," are injected on an AGILENT 1200SL binary gradient, liquid chromatography, coupled to an AGILENT 6520 QTof, quadruple-time of flight MS system, via a dual spray electrospray (ESI) interface, operating in the PI mode. The following analysis conditions are used: column: 150×4.6 mm ID, 3.5 µm ZORBAX SB-C8; column temperature: 40° C.; mobile phase: 75/25 A/B to 15/85 A/B at 40 minutes; solvent A=0.1 v % formic acid in water; solvent B=THF;

flow 1.0 mL/min; UV detection: diode array 210 to 600 nm (extracted wavelength 250,280 nm); ESI conditions: gas temperature 365° C.; gas flow—8 ml/min; capillary—3.5 kV; nebulizer—40 PSI; fragmentor—145V.

DSC is performed using a 2,000 instrument at a scan rate of 10° C./min, and in a nitrogen atmosphere for all cycles. The sample (about 7-10 mg) is scanned from room temperature to 300° C., cooled to −60° C., and reheated to 300° C. The glass transition temperature ($T_g$) is measured on the second heating scan. Data analysis is performed using TA Universal Analysis software. The $T_g$ is calculated using the "mid-point of inflection" methodology.

2. Modeling

All computations utilized the Gaussian09 program[1]. The calculations are performed with the hybrid density functional theory (DFT) method, B3LYP[2], and the 6-31G* basis set.[3] The singlet state calculations used the closed shell approximation, and the triplet state calculations used the open shell approximation. All values are quoted in electron-volts (eV). The HOMO and LUMO values are determined from the orbital energies of the optimized geometry of the singlet ground state. The triplet energies are determined as the difference between the total energy of the optimized triplet state and the optimized singlet state. The singlet-triplet gap is the energy difference between the first triplet state ($T_1$) and the singlet state ($S_1$), computed on the optimized triplet geometry, using time dependent density functional theory (TDDFT).

1. Gaussian 09, Revision A.02, Frisch, M. J.; Trucks, G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenberg, J. L.; Hada, M.; Ehara, M.; Toyota, K.; Fukuda, R.; Hasegawa, J.; Ishida, M.; Nakajima, T.; Honda, Y.; Kitao, O.; Nakai, N.; Vreven, T.; Montgomery, Jr., J. A.; Peralta, J. E.; Ogliaro, F.; Bearpark, M.; Heyd, J. J.; Brothers, E.; Kudin, K. N.; Staroverov, V. N.; Kobayashi, R.; Normand, J.; Raghavachari, K.; Rendell, A.; Burant, J. C.; Iyengar, S. S.; Tomasi, J.; Cossi, M.; Rega, N.; Millam, J. M.; Klene, M.; Knox, J. E.; Cross, J. B.; Bakken, V.; Adamo, C.; Jaramillo, J.; Gomperts, R.; Stratmann, R. E.; Yazyev, O.; Austin, A. J.; Cammi, R.; Pomelli, C.; Ochterski, J. W.; Martin, R. L.; Morokuma, K.; Zakrzewski, V. G.; Voth, G. A.; Salvador, P.; Dannenberg, J. J.; Dapprich, S.; Daniels, A. D.; Farkas, O.; Foresman, J. B.; Ortiz, J. V.; Cioslowski, J.; Fox, D. J., Gaussian, Inc., Wallingford Conn., 2009.

2. (a) Becke, A. D. *J. Chem. Phys.* 1993, 98, 5648. (b) Lee, C.; Yang, W.; Parr, R. G. *Phys. Rev B* 1988, 37, 785. (c) Miehlich, B.; Savin, A.; Stoll, H.; Preuss, H. *Chem. Phys. Lett.* 1989, 157, 200.

3. (a) Ditchfield, R.; Hehre, W. J.; Pople, J. A. *J. Chem. Phys.* 1971, 54, 724. (b) Hehre, W. J.; Ditchfield, R.; Pople, J. A. *J. Chem. Phys.* 1972, 56, 2257. (c) Gordon, M. S. *Chem. Phys. Lett.* 1980, 76, 163.

TABLE 1

HOMO, LUMO, Triplet and S1-T1 gap values as calculated by B3LYP/6-31G* method

| | HOMO (eV) | LUMO (eV) | $T_1$ (eV) | $S_1$-$T_1$ Gap (eV) |
|---|---|---|---|---|
| Structure (ii) | −4.88 | −1.84 | 3.04 | 0.03 |
| Structure (iii) | −4.74 | −1.82 | 2.94 | 0.05 |
| Structure (iv) | −4.83 | −1.86 | 2.99 | 0.02 |
| Structure (v) | −4.69 | −1.85 | 2.92 | 0.03 |
| Structure (ix) | −4.80 | −1.80 | 2.90 | 0.03 |

TABLE 1-continued

HOMO, LUMO, Triplet and S1-T1 gap values as calculated by B3LYP/6-31G* method

| | HOMO (eV) | LUMO (eV) | $T_1$ (eV) | $S_1$-$T_1$ Gap (eV) |
|---|---|---|---|---|
| Structure (x) | −4.75 | −1.98 | 2.79 | 0.04 |
| Structure (xi) | −4.87 | −1.84 | 3.01 | 0.01 |
| Structure (xii) | −5.03 | −1.79 | 3.02 | 0.16 |
| Structure (xiii) | −5.18 | −1.82 | 3.11 | 0.08 |
| Structure (xv) | −4.83 | −1.23 | 3.16 | 0.20 |
| Structure (xvi) | −4.90 | −1.57 | 2.98 | 0.29 |
| Structure (xvii) | −4.92 | −1.52 | 3.03 | 0.32 |
| Structure (xviii) | −4.97 | −1.31 | 3.06 | 0.20 |
| Structure (xix) | −4.65 | −1.65 | 2.64 | 0.38 |

3. Syntheses

Example 1. Synthesis of Structure (ii)

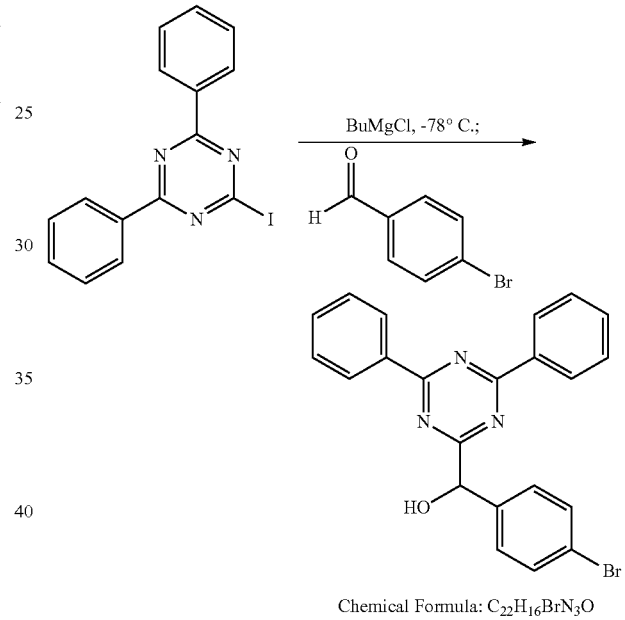

Chemical Formula: $C_{22}H_{16}BrN_3O$
Exact Mass: 417.05
Molecular Weight: 418.29

(4-bromophenyl)(4,6-diphenyl-1,3,5-triazin-2-yl)methanol

A 50 mL three neck, round bottom flask, equipped with a stir bar and nitrogen inlet, is charged with iododiphenyl triazine (Peng, Z.; Haag, B. A.; Knochel, P. Org. Lett. 2010, 12, 5398) (4.7 g, 13.09 mmol) and anhydrous tetrahydrofuran (THF, 13 mL), and the flask is cooled with a dry ice/acetone bath. Butylmagnesium chloride (2M in THF, 7.5 mL, 15 mmol) is added over 5 minutes, and the mixture is stirred at −78° C. for 30 minutes. 4-Bromobenzaldehyde (2.79 g, 15.08 mmol) is added, and the dry ice bath removed. The reaction initially turned dark, but over one hour turned light yellow. The reaction is quenched after two hours at room temperature with brine, and extracted with dichloromethane (3×). A rag layer is separated with the organic layer, leaving water in this layer. The combined organic layers are dried over magnesium sulfate, filtered, and concentrated by rotary evaporation. The crude material is dry loaded onto silica gel, and purified on the CombiFlash (ethyl acetate/hexanes). Fractions 1B-4C are collected, giving the titled compound as white solids (2.36 g, 5.64 mmol, 43%).

¹H NMR (400 MHz, Chloroform-d) δ 8.67-8.59 (m, 4H), 7.68-7.59 (m, 2H), 7.59-7.52 (m, 6H), 7.53-7.43 (m, 2H), 5.87 (d, J=5.7 Hz, 1H), 4.97 (d, J=5.8 Hz, 1H).

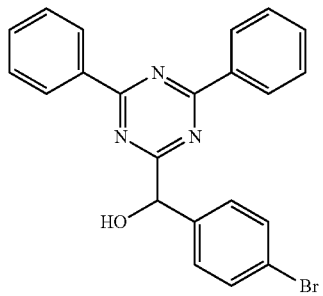

Chemical Formula: C₂₂H₁₆BrN₃O
Exact Mass: 417.05
Molecular Weight: 418.29

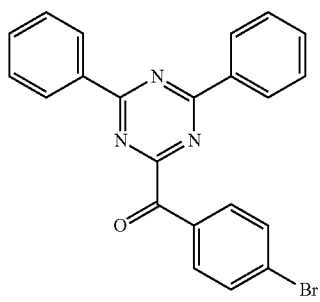

Chemical Formula: C₂₂H₁₄BrN₃O
Exact Mass: 415.03
Molecular Weight: 416.28

(4-bromophenyl)(4,6-diphenyl-1,3,5-triazin-2-yl)methanone

A 250 mL flask with nitrogen inlet is charged with secondary alcohol (2.3 g, 5.5 mmol) and dichloromethane (65 mL) giving a clear solution. Manganese dioxide (2.9 g) is added and the reaction stirred for 4 hours (h) at room temperature. The mixture is filtered through celite and washed with dichloromethane. The filtrate is concentrated by rotary evaporation giving a white solid (1.92 g, 84%). No further purification is done.

¹H NMR (400 MHz, Chloroform-d) δ 8.72-8.66 (m, 4H), 8.06-7.98 (m, 2H), 7.72-7.66 (m, 2H), 7.67-7.60 (m, 2H), 7.60-7.53 (m, 4H).

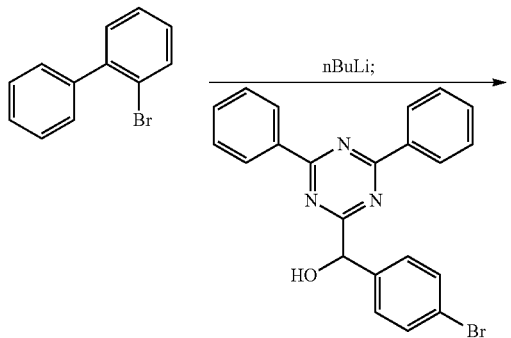

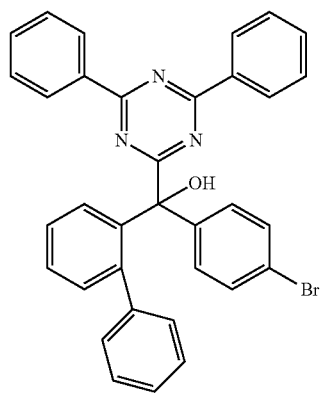

Chemical Formula: C₃₄H₂₄BrN₃O
Exact Mass: 569.11
Molecular Weight: 570.49

[1,1'-biphenyl]-2-yl(4-bromophenyl)(4,6-diphenyl-1,3,5-triazin-2-yl)methanol

A 100 mL three neck round bottom flask is charged with 2-bromobiphenyl (0.760 g, 3.26 mmol) and anhydrous THF (40 mL) and is cooled to −78° C. 1.6M n-butyllithium in hexanes (1.9 mL, 3.04 mmol) is added over 5 minutes and the reaction stirred at −78° C. for 30 min. Ketone (1.14 g, 2.74 mmol) in 20 mL anhydrous THF is added to the lithiated species forming a dark mixture. After 15 min at −78° C. the ice bath is removed and the reaction is stirred at room temperature for 2 h. Water, 2N HCl, and dichloromethane is added to the reaction. The aqueous layer is backextracted 1× with dichloromethane and the combined organic layers are dried over magnesium sulfate, filtered and concentrated giving 1.86 g of a yellow solid that is carried into the next reaction without purification.

¹H NMR (400 MHz, Chloroform-d) δ 8.45-8.35 (m, 4H), 7.86 (d, J=8.7 Hz, 2H), 7.63-7.55 (m, 4H), 7.54-7.47 (m, 4H), 7.47-7.38 (m, 5H), 7.39-7.32 (m, 2H), 7.14 (dd, J=7.6, 1.6 Hz, 2H).

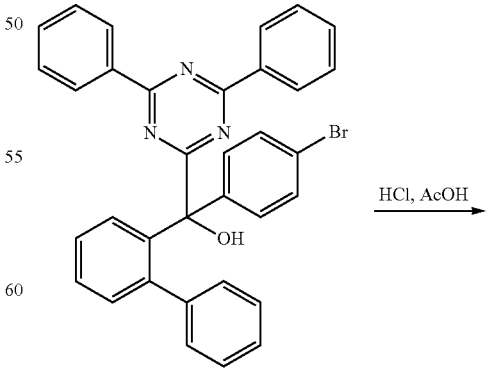

Chemical Formula: C₃₄H₂₄BrN₃O
Exact Mass: 569.11
Molecular Weight: 570.48

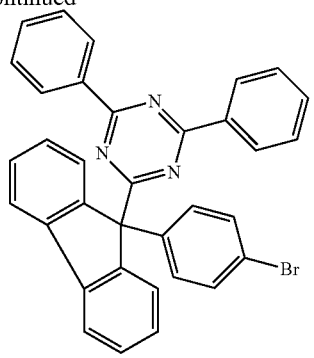

Chemical Formula: C₃₄H₂₂BrN₃
Exact Mass: 551.10
Molecular Weight: 552.47

2-(9-(4-bromophenyl)-9H-fluoren-9-yl)-4,6-diphenyl-1,3,5-triazine

The tertiary alcohol (1.86 g) is dissolved in dichloromethane, and transferred to a 100 mL three neck, round bottom flask, and the dichloromethane is blown off with nitrogen. The flask is equipped with a stir bar, thermocouple, heating mantle, and condenser with nitrogen inlet. Acetic acid (40 mL) and concentrated hydrochloric acid (1 mL) are added to the solid, forming an insoluble mixture. The reaction is heated to 112° C. for 17 hours (the material dissolved over the first 30 minutes of heating). The reaction is allowed to cool to room temperature, and is poured into 300 mL of water, causing material to crash out. Dichloromethane (300 mL) is used to do a first extraction, and the layers are separated. The aqueous layer is back extracted with dichloromethane (3×100 mL), and the combined organic layers are dried over magnesium sulfate, filtered, and concentrated by rotary evaporation. The crude material is dissolved in dichloromethane, and concentrated onto silica gel, and purified on the CombiFlash to give the titled compound as white/pink solids (0.61 g, 1.1 mmol, 40% over 2 steps).

$^1$H NMR (400 MHz, Chloroform-d) δ 8.59-8.49 (m, 4H), 7.88 (ddd, J=7.6, 1.2, 0.7 Hz, 2H), 7.79 (ddd, J=7.6, 1.3, 0.6 Hz, 2H), 7.59-7.52 (m, 2H), 7.52-7.46 (m, 4H), 7.43 (td, J=7.5, 1.2 Hz, 2H), 7.37 (td, J=7.5, 1.3 Hz, 2H), 7.32 (d, J=8.6 Hz, 2H), 6.96 (d, =8.6 Hz, 2H). 13C NMR (101 MHz, CDCl3) δ 171.28, 143.93, 140.83, 135.90, 132.65, 131.46, 129.19, 129.01, 128.64, 128.16, 127.45, 119.93.

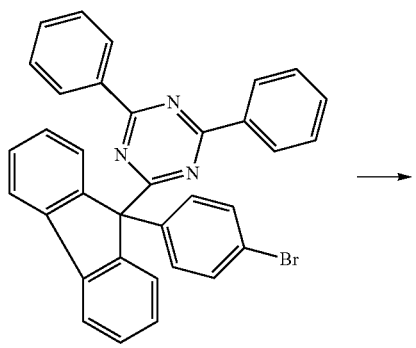

Chemical Formula: C₃₄H₂₂BrN₃
Exact Mass: 551.10
Molecular Weight: 552.47

→

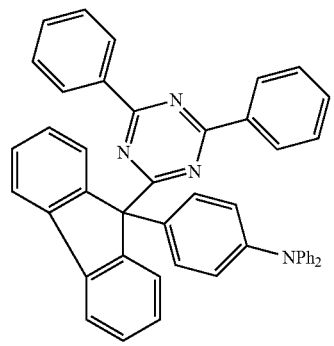

Example 1
Chemical Formula: C₄₆H₃₂N₄
Exact Mass: 640.26
Molecular Weight: 640.79

Structure (ii) (Ph=phenyl) 4-(9-(4,6-diphenyl-1,3,5-triazin-2-yl)-9H-fluoren-9-yl)-N,N-diphenylaniline Aryl bromide (0.610 g, 1.1 mmol) is transferred into a 100 mL, 3 neck, round bottomed flask, as a dichloromethane solution, and the dichloromethane is blown off with a stream of nitrogen. Diphenylamine (0.187, 1.1 mmol), sodium tert-butoxide (0.161 g, 1.7 mmol), and Pd(crotyl)(PtBu3)Cl (0.020 g, 0.05 mmol) are added, and the flask is equipped with a thermocouple, stir bar, and water condenser with nitrogen inlet. Toluene (60 mL) that had been sparged with nitrogen for 5 minutes, is added, and the reaction heated to 110° C. for 2 hours. The reaction is allowed to cool to room temperature, and is filtered through a pad of silica gel, and washed with dichloromethane. The material is dissolved in dichloromethane (~40 mL), and acetone is added (~50 mL), and the mixture is stirred at room temperature for 30 minutes, over which time, solids started to form. More acetone (~40 mL) is added, and the mixture is placed in a refrigerator for 2 hours, and then filtered and washed with acetone, giving the titled compound as off white solids (0.367 g, 52%, ~98% purity by HPLC). The filtrate is concentrated on a rotovap to ~10 mL, and is cooled to room temperature, forming more solids that are isolated by filtration. The pale yellow solids are washed with acetone, giving a second crop of material (0.154 g, 22%, ~90% pure by HPLC).

$^1$H NMR (400 MHz, Chloroform-d) δ 8.62-8.53 (m, 4H), 8.07-8.00 (m, 2H), 7.81-7.74 (m, 2H), 7.60-7.53 (m, 2H), 7.50 (ddt, J=8.4, 6.6, 1.5 Hz, 4H), 7.46-7.36 (m, 4H), 7.22-7.15 (m, 4H), 7.07-7.00 (m, 4H), 7.00-6.91 (m, 4H), 6.90-6.84 (m, 2H).

13C NMR (101 MHz, CDCl3) δ 180.14, 171.10, 148.06, 147.62, 146.26, 140.79, 138.40, 136.12, 132.51, 129.14, 129.03, 128.60, 128.53, 128.07, 127.90, 127.16, 124.37, 123.20, 122.76, 119.73, 67.42.

Example 2. Synthesis of Structure (ix)

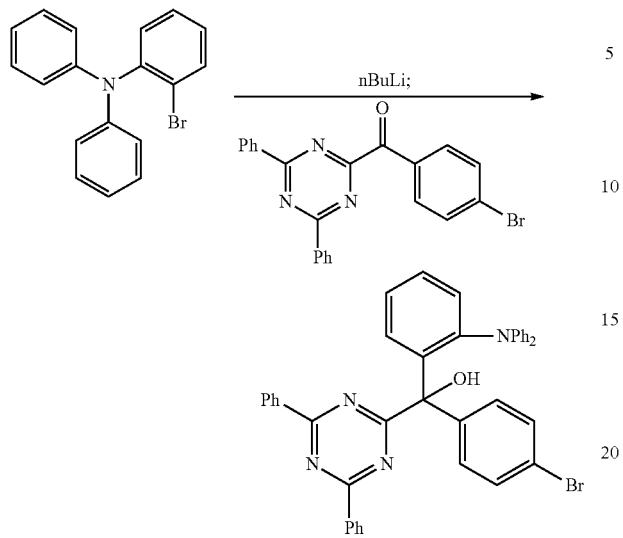

(4-bromophenyl)(4,6-diphenyl-1,3,5-triazin-2-yl)(2-(diphenylamino)phenyl)methanol A 50 mL three neck round bottom flask is charged with (2-bromophenyl)diphenylamine (0.527 g, 1.63 mmol) and anhydrous THF (20 mL) and is cooled to −78° C. 1.6M n-butyllithium in hexanes (1.0 mL, 1.6 mmol) is added over 5 minutes and the reaction stirred at −78° C. for 30 min. Ketone (0.547 g, 1.31 mmol) in 10 mL anhydrous THF is added to the lithiated species forming a dark mixture. After 5 min at −78° C. the ice bath is removed and the yellow reaction stirred at room temperature for overnight (complete at 1.5 h). Water, 2N HCl, and dichloromethane is added to the reaction. The aqueous layer is backextracted 1× with dichloromethane and the combined organic layers are dried over magnesium sulfate, filtered and concentrated giving a yellow solid that is carried into the next reaction without purification.

$^1$H NMR (400 MHz, Chloroform-d) δ 8.52-8.43 (m, 4H), 7.86 (d, J=8.7 Hz, 2H), 7.64-7.56 (m, 2H), 7.55-7.48 (m, 4H), 7.45 (d, J=8.7 Hz, 2H), 7.35 (ddd, J=7.8, 6.9, 2.0 Hz, 1H), 7.25-7.18 (m, 1H), 7.12-7.03 (m, 4H), 7.00-6.92 (m, 2H), 6.76-6.68 (m, 2H), 6.63-6.56 (m, 2H), 6.55-6.43 (m, 2H).

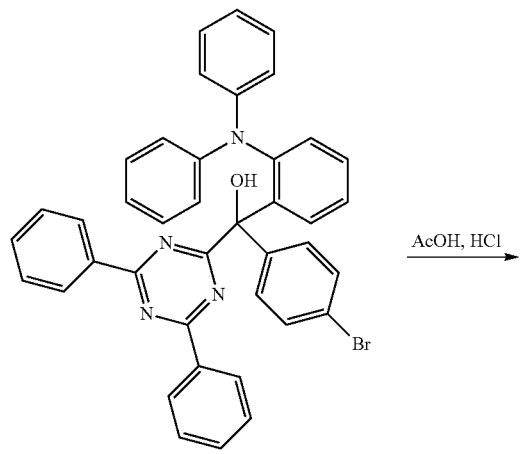

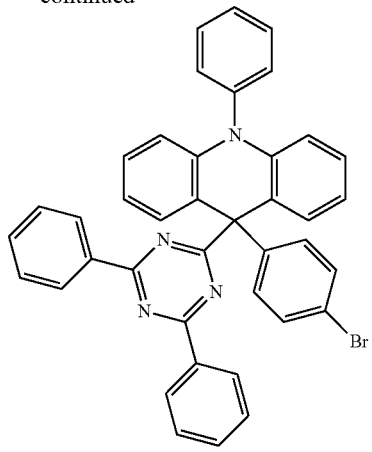

9-(4-bromophenyl)-9-(4,6-diphenyl-1,3,5-triazin-2-yl)-10-phenyl-9,10-dihydroacridine Tertiary alcohol is dissolved in dichloromethane and transferred to a 50 mL three neck round bottom flask and the dichloromethane is blown off with nitrogen. The flask is equipped with a stir bar, thermocouple, heating mantle, and condenser with nitrogen inlet. Acetic acid (20 mL) and concentrated hydrochloric acid (0.5 mL) is added to the solid forming an insoluble mixture. The reaction is heated up to 112° C. for 5 h (the material dissolved over the first 1 h of heating turning dark green over the course of the reaction). The reaction is allowed to cool to room temperature. Dichloromethane and water are added and the layers are separated. The aqueous layer is back extracted with dichloromethane and the combined organic layers are washed with 10 wt % NaOH turning the green solution dark yellow. The combined organic layers dried over magnesium sulfate, filtered, and concentrated. The crude material is concentrated onto silica gel and purified by flash chromatography (dichloromethane/hexanes) giving 0.80 g product, 89% over two steps.

$^1$H NMR (400 MHz, Chloroform-d) δ 8.48-8.40 (m, 4H), 7.59-7.50 (m, 4H), 7.50-7.41 (m, 7H), 7.34-7.26 (m, 2H), 7.25-7.19 (m, 2H), 7.09-6.97 (m, 4H), 6.83 (ddd, J=7.8, 7.2, 1.2 Hz, 2H), 6.35 (dd, J=8.3, 1.2 Hz, 2H).

$^{13}$C NMR (101 MHz, CDCl$_3$) δ 171.24, 145.94, 141.59, 140.85, 136.01, 132.74, 132.52, 131.37, 131.26, 130.74, 130.69, 128.99, 128.59, 128.29, 127.47, 125.76, 120.50, 120.14, 114.03.

-continued

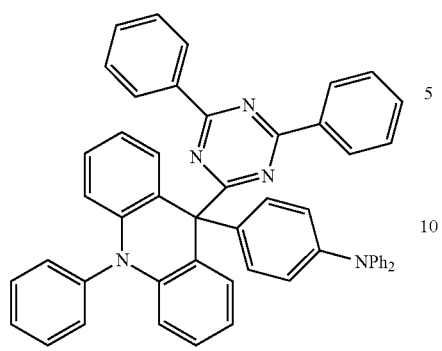

Structure (ix) (Ph=phenyl) 4-(9-(4,6-diphenyl-1,3,5-triazin-2-yl)-10-phenyl-9,10-dihydroacridin-9-yl)-N,N-diphenylaniline Aryl bromide (0.8 g, 1.2 mmol) is transferred into a 250 mL 3 neck round bottomed flask as a dichloromethane solution and the dichloromethane is blown off with a stream of nitrogen. Diphenylamine (0.217, 1.3 mmol), sodium tert-butoxide (0.187 g, 1.9 mmol), and Pd(crotyl)(PtBu3)Cl (Colacot, T. J. et al, *J. Org. Chem.* 2011, 76, 7918-7932) (0.025 g, 0.06 mmol) is added and the flask is equipped with a thermocouple, stir bar, and water condenser with nitrogen inlet. Toluene (68 mL) that had been sparged with nitrogen for 5 minutes is added and the reaction heated to 110° C. for 1 h. The reaction is allowed to cool to room temperature and is partitioned between dichloromethane and water. The organic layer is dried over magnesium sulfate, filtered, and concentrated. The material is purified by flash chromatography (dichloromethane/hexanes) to provide the titled compound as white solids. Acetone (~15 mL) is added and the solids are isolated by filtration washing with acetone (0.52 g, 0.7 mmol, 57%).

$^1$H NMR (400 MHz, Chloroform-d) δ 8.49-8.39 (m, 4H), 7.59-7.49 (m, 4H), 7.49-7.40 (m, 5H), 7.29-7.21 (m, 4H), 7.21-7.12 (m, 9H), 7.08-6.97 (m, 7H), 6.89 (ddd, J=7.7, 7.1, 1.2 Hz, 2H), 6.36 (dd, J=8.3, 1.2 Hz, 2H).

$^{13}$C NMR (101 MHz, CDCl$_3$) δ 171.08, 141.72, 132.38, 131.41, 131.37, 130.64, 129.20, 129.02, 128.53, 127.20, 124.37, 122.75, 122.58, 119.97, 113.93.

Example 3. Synthesis of Structure (x)

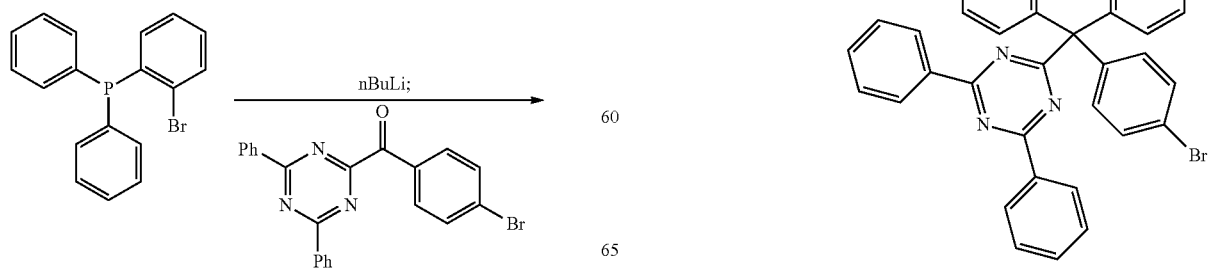

-continued

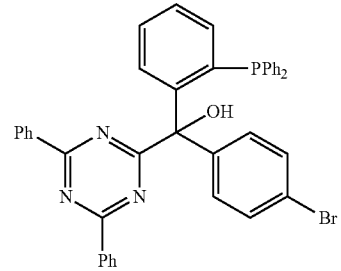

(4-bromophenyl)(4,6-diphenyl-1,3,5-triazin-2-yl)(2-(diphenylphosphinyl)phenyl)methanol A 50 mL three neck round bottom flask is charged with (2-bromophenyl)diphenylphosphine (0.5 g, 1.47 mmol) and anhydrous THF (20 mL) and is cooled to −78° C. 1.6M n-butyllithium in hexanes (1 mL, 1.6 mmol) is added over 5 minutes and the reaction stirred at −78° C. for 30 min. Ketone (0.555 g, 1.33 mmol) in THF (10 mL) is added to the lithiated species forming a dark mixture. After 5 min at −78° C. the ice bath is removed and the reaction stirred at room temperature for 3 h. The reaction is partitioned between dichloromethane and water. The organic layer is dried over magnesium sulfate, filtered, and concentrated giving a sticky oil. The material is taken into the next reaction without further purification.

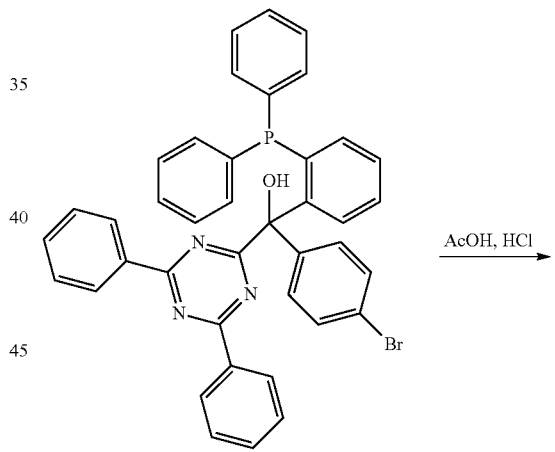

10-(4-bromophenyl)-10-(4,6-diphenyl-1,3,5-triazin-2-yl)-5-phenyl-10H-acridophosphine 5-oxide Tertiary alcohol is dissolved in dichloromethane and transferred to a 50 mL three neck round bottom flask and the dichloromethane is blown off with nitrogen. The flask is equipped with a stir bar, thermocouple, heating mantle, and condenser with nitrogen inlet. Acetic acid (20 mL) and concentrated hydrochloric acid (0.5 mL) is added to the solid forming an insoluble mixture. The reaction is heated up to 112° C. for 17 h (the material dissolved over the first 1 h). The reaction is allowed to cool to room temperature. Dichloromethane and water are added and the layers are separated. The organic layer is washed with sat. sodium bicarbonate and the organic layer is dried over magnesium sulfate, filtered, and concentrated. The material is purified by flash chromatography (methanol/dichloromethane) giving the titled compound as an off white solid (0.450 g, 0.066 mmol, 59%).

$^1$H NMR (400 MHz, Chloroform-d) δ 8.47-8.40 (m, 4H), 7.78 (dd, J=7.9, 4.1 Hz, 1H), 7.65 (ddd, J=11.9, 8.2, 1.4 Hz, 2H), 7.60-7.37 (m, 10H), 7.36-7.30 (m, 2H), 7.23-7.16 (m, 3H), 7.12-7.02 (m, 1H), 7.01 (d, J=1.2 Hz, 1H), 7.00-6.92 (m, 3H). $^{31}$P NMR (162 MHz, CDCl$_3$) δ 32.06.

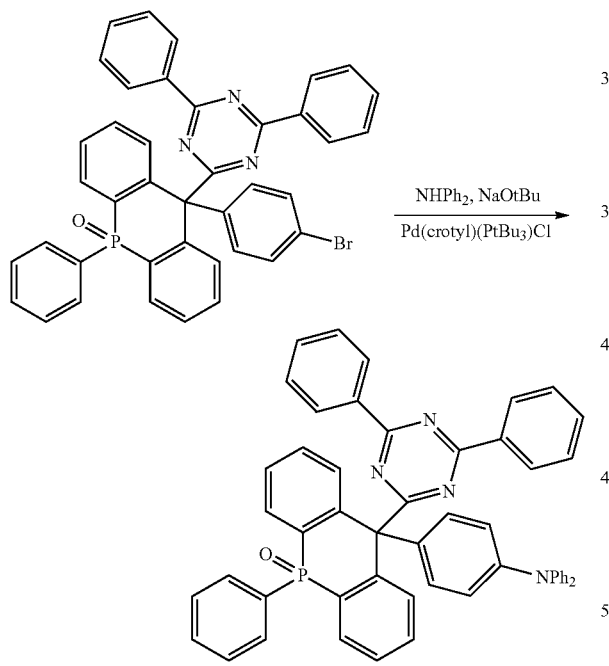

Structure (x) (Ph=phenyl) 10-(4,6-diphenyl-1,3,5-triazin-2-yl)-10-(4-(diphenylamino)phenyl)-5-phenyl-10H-acridophosphine 5-oxide Aryl bromide (0.45 g, 0.7 mmol) is transferred into a 100 mL 3 neck round bottomed flask as a dichloromethane solution and the dichloromethane is blown off with a stream of nitrogen. Diphenylamine (0.121 g, 0.7 mmol), sodium tert-butoxide (0.096 g, 1.0 mmol), and Pd(crotyl)(PtBu3)Cl (Colacot, T. J. et al, *J. Org. Chem.* 2011, 76, 7918-7932) (0.014 g, 0.04 mmol) is added and the flask is equipped with a thermocouple, stir bar, and water condenser with nitrogen inlet. Toluene (40 mL) that had been sparged with nitrogen for 5 minutes is added and the reaction heated to 110° C. for 2 h. The reaction is allowed to cool to room temperature and is partitioned between dichloromethane and water. The organic layer is dried over magnesium sulfate, filtered, and concentrated. The material is purified by flash chromatography (ethyl acetate/dichloromethane) providing the titled compound (0.07 g, 14%).

$^1$H NMR (400 MHz, Chloroform-d) δ 8.49-8.39 (m, 4H), 7.98-7.92 (m, 1H), 7.73-7.64 (m, 2H), 7.64-7.58 (m, 1H), 7.58-7.53 (m, 2H), 7.52-7.39 (m, 7H), 7.24-7.13 (m, 7H), 7.08 (ddd, J=14.2, 7.8, 1.4 Hz, 1H), 7.05-7.00 (m, 4H), 6.99-6.88 (m, 8H). $^{31}$P NMR (162 MHz, CDCl$_3$) δ 31.78.

Example 4. Synthesis of Structure (xv)

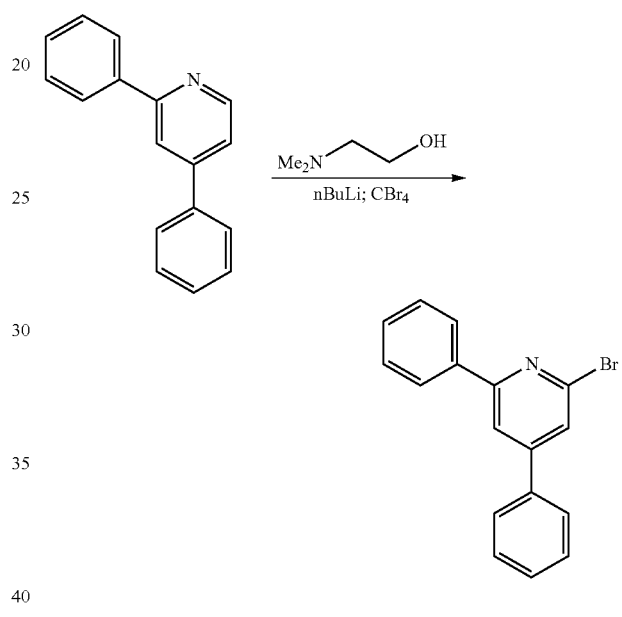

2-bromo-4,6-diphenylpyridine

A 3-neck 500 mL round bottom flask equipped with a nitrogen inlet and stir bar is charged with 2-dimethylaminoethanol (4.0 mL, 39.76 mmol) and hexanes (40 mL). The flask is then cooled to 0° C. with an ice water mixture. N-Butyllithium (1.6 M in hexanes, 48 mL, 76.8 mmol) is then added keeping the internal temperature <5° C. The mixture is allowed to stir at 0° C. for 30 min. In a 20 ml vial 2,4-diphenylpyridine (3.0092 g, 13.01 mmol) is dissolved in hexanes (10 mL) and is then added to the n-butyllithium solution keeping the temperature <5° C. The reaction mixture is then allowed to stir at 0° C. for 1 h. The temperature is then lowered to −69° C. using dry ice/acetone mixture. Tetrabromomethane (30.12 g, 90.82 mmol) in hexanes (45 mL) is then added slowly keeping the internal temperature <−50° C. The mixture is then allowed to stir for 1 h at −70° C. The dry ice/acetone mixture is then removed and the RBF is allowed to warm to room temperature. After 1 h flask is cooled back down to 0° C. and hydrolysis is done by adding 50 mL of water (15° C. exotherm observed). The mixture is then poured into a separatory funnel and extracted with methylene chloride. The combined organic layers are dried over magnesium sulfate, filtered, and concentrated by rotary evaporation. The crude material is dry loaded onto silica gel and purified by flash chromatography (hexanes/ethyl acetate) to provide the titled compound (3.35 g, 10.8 mmol, 83%).

$^1$H NMR (400 MHz, Chloroform-d) δ 8.06-8.01 (m, 2H), 7.86 (d, J=1.4 Hz, 1H), 7.68-7.63 (m, 2H), 7.62 (d, J=1.4 Hz, 1H), 7.55-7.40 (m, 6H).

$^{13}$C NMR (101 MHz, CDCl$_3$) δ 158.88, 151.96, 142.78, 137.84, 137.24, 129.65, 129.59, 129.28, 129.24, 128.89, 128.82, 127.24, 127.12, 124.20, 117.56.

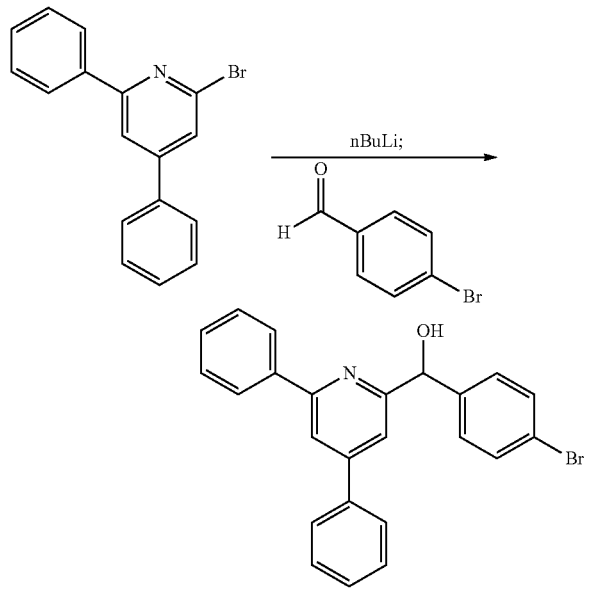

(4-bromophenyl)(4,6-diphenylpyridin-2-yl)methanol

A 50 mL three necked round bottomed flask equipped with a thermocouple and a stir bar is charged with 2-bromo-4,6-diphenylpyridine (0.45 g, 1.45 mmol) and anhydrous THF (15 mL) and is cooled to <−60° C. with a dry ice/acetone bath. n-Butyllithium (1.6M in hexanes, 0.9 mL, 1.44 mmol) is added dropwise over ~5 minutes keeping the temperature below −55° C. The solution turned black. After 30 minutes at <−60° C. 4-bromobenzaldehyde (0.275, 1.49 mmol) is added and the ice bath removed. After 20 minutes the reaction is complete but it is allowed to stir overnight at room temperature before quenching with water (~10 mL) and 2M HCl (~5 mL). The layers are separated and the aqueous layer backextracted with dichloromethane. The combined organic layers are dried over magnesium sulfate, filtered and concentrated by rotary evaporation. The crude dark red oil is dissolved in acetone and concentrated onto silica gel and is purified by flash chromatography (hexanes/ethyl acetate) to provide the titled compound as a yellow oil (0.36 g, 0.86 mmol, 60%).

$^1$H NMR (400 MHz, Chloroform-d) δ 8.14-8.07 (m, 2H), 7.89-7.82 (m, 1H), 7.63-7.56 (m, 2H), 7.56-7.39 (m, 8H), 7.39-7.34 (m, 2H), 7.21 (dd, J=1.4, 0.6 Hz, 1H), 5.81 (s, 1H).

$^{13}$C NMR (101 MHz, CDCl$_3$) δ 160.51, 156.12, 150.70, 138.57, 138.21, 131.74, 129.46, 129.28, 129.13, 128.94, 128.86, 128.77, 127.16, 127.10, 127.05, 121.85, 117.84, 117.78.

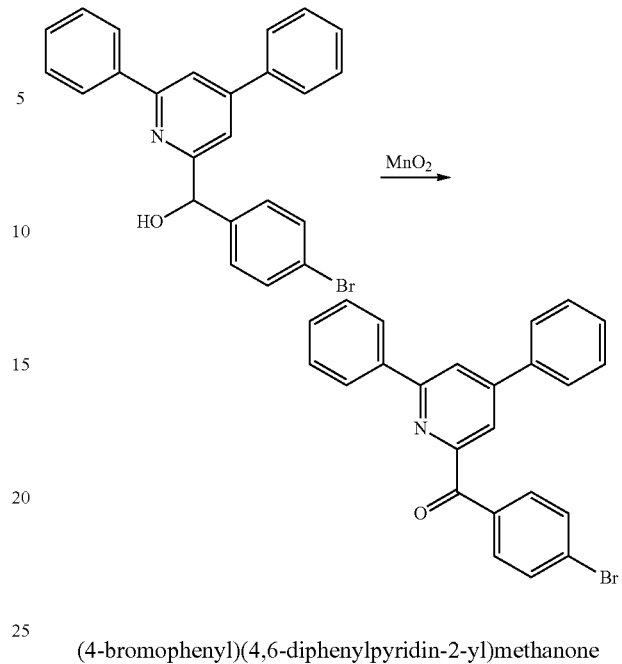

(4-bromophenyl)(4,6-diphenylpyridin-2-yl)methanone

A 40 mL vial equipped with a stir bar is charged with secondary alcohol (0.36 g, 0.86 mmol), dichloromethane (10 mL), and manganese (IV) oxide (0.48, 5.52 mmol). The vial is sealed and stirred at room temperature overnight. The reaction is filtered through a pad of celite washing with dichloromethane (~120 mL). The material is concentrated by rotary evaporation giving a pale yellow solid (0.30 g, 0.72 mmol, 84%). The material is carried into the next reaction without purification.

$^1$H NMR (400 MHz, Chloroform-d) δ 8.25 (d, J=1.6 Hz, 1H), 8.19-8.13 (m, 3H), 8.10-8.05 (m, 2H), 7.81-7.75 (m, 2H), 7.69-7.65 (m, 2H), 7.59-7.42 (m, 6H).

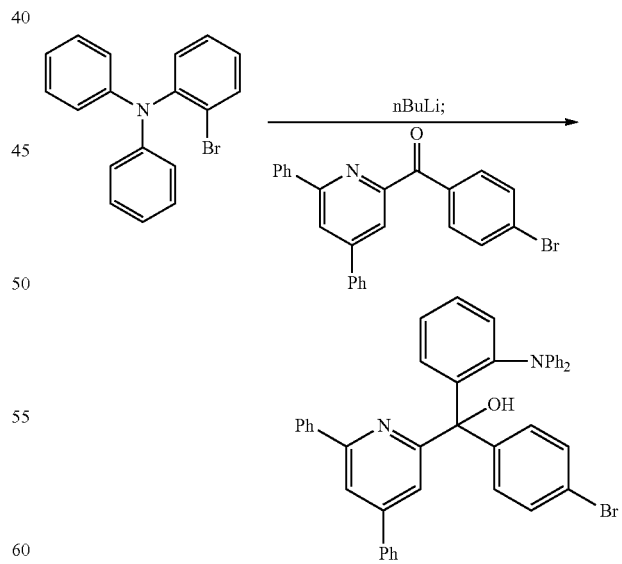

(4-bromophenyl)(2-(diphenylamino)phenyl)(4,6-diphenylpyridin-2-yl)methanol

A 50 mL three neck round bottom flask is charged with (2-bromophenyl)diphenylamine (0.255 g, 0.79 mmol) and anhydrous THF (10 mL) and is cooled to −78° C. 1.6M n-butyllithium in hexanes (0.5 mL, 0.8 mmol) is added over 5 minutes and the reaction stirred at −78° C. for 30 min. Ketone (0.3 g, 0.72 mmol) in 5 mL anhydrous THF is added to the lithiated species forming a dark mixture. After 5 min at −78° C. the ice bath is removed and the yellow reaction stirred at room temperature for 1.5 h. Water, 2N HCl, and dichloromethane is added to the reaction. The aqueous layer is backextracted 1× with dichloromethane and the combined organic layers are dried over magnesium sulfate, filtered and concentrated giving a yellow solid that is carried into the next reaction without purification.

combined organic layers dried over magnesium sulfate, filtered, and concentrated. The crude material is concentrated onto silica gel and purified by flash chromatography (hexanes/dichloromethane) giving 0.360 g product, 78% over two steps.

$^1$H NMR (400 MHz, Chloroform-d) δ 7.98-7.90 (m, 2H), 7.81 (d, J=1.4 Hz, 1H), 7.60-7.32 (m, 13H), 7.22-7.15 (m, 2H), 7.14-7.08 (m, 2H), 7.08-6.98 (m, 5H), 6.92-6.82 (m, 2H), 6.37 (dd, J=8.3, 1.2 Hz, 2H).

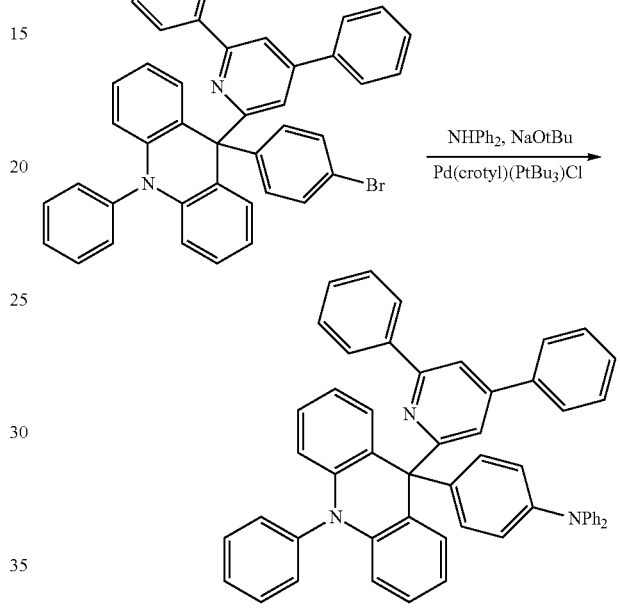

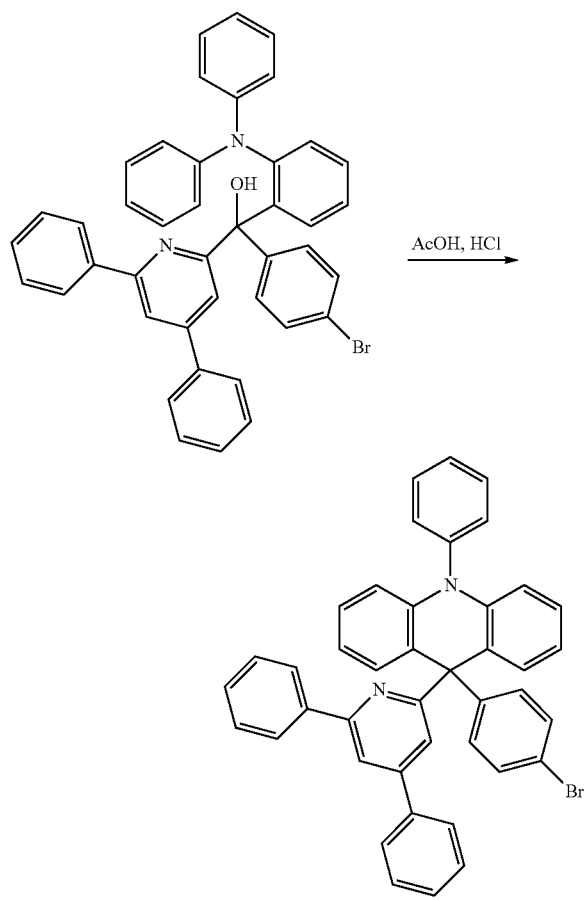 [SMILES: OC(c1ccc(Br)cc1)(c1cc(-c2ccccc2)cc(-c2ccccc2)n1)c1ccccc1N(c1ccccc1)c1ccccc1 ; Brc1ccc(C2(c3cc(-c4ccccc4)cc(-c4ccccc4)n3)c3ccccc3N(c3ccccc3)c3ccccc32)cc1]

9-(4-bromophenyl)-9-(4,6-diphenylpyridin-2-yl)-10-phenyl-9,10-dihydroacridine

Tertiary alcohol is dissolved in dichloromethane and transferred to a 50 mL three neck round bottom flask and the dichloromethane is blown off with nitrogen. The flask is equipped with a stir bar, thermocouple, heating mantle, and condenser with nitrogen inlet. Acetic acid (10 mL) and concentrated hydrochloric acid (0.25 mL) is added to the solid forming an insoluble mixture. The reaction is heated up to 112° C. for 15 h (the material dissolved over the first 1 h of heating turning dark green over the course of the reaction). The reaction is allowed to cool to room temperature. Dichloromethane and water are added and the layers are separated. The aqueous layer is back extracted with dichloromethane and the combined organic layers are washed with 10 wt % NaOH turning the green solution dark yellow. The Structure (xv) (Ph=phenyl) 4-(9-(4,6-diphenylpyridin-2-yl)-10-phenyl-9,10-dihydroacridin-9-yl)-N,N-diphenylaniline Aryl bromide (0.36 g, 0.6 mmol) is transferred into a 100 mL 3 neck round bottomed flask as a dichloromethane solution and the dichloromethane is blown off with a stream of nitrogen. Diphenylamine (0.100, 0.6 mmol), sodium tert-butoxide (0.083 g, 0.9 mmol), and Pd(crotyl)(PtBu3)Cl (0.012 g, 0.03 mmol) is added and the flask is equipped with a thermocouple, stir bar, and water condenser with nitrogen inlet. Toluene (28 mL) that had been sparged with nitrogen for 5 minutes is added and the reaction heated to 110° C. for 3 h. The reaction is allowed to cool to room temperature and is filtered through a pad of silica gel washing with dichloromethane. The material is purified by flash chromatography (0 to 30% dichloromethane/hexanes) to provide the titled compound as pale yellow solids (0.15 g, 0.205 mmol, 34%).

$^1$H NMR (400 MHz, Chloroform-d) δ 7.97-7.90 (m, 2H), 7.80 (d, J=1.4 Hz, 1H), 7.58-7.48 (m, 4H), 7.48-7.31 (m, 7H), 7.27-7.19 (m, 4H), 7.19-7.08 (m, 9H), 7.07-6.95 (m, 8H), 6.90 (td, J=7.5, 1.3 Hz, 2H), 6.40 (dd, J=8.2, 1.1 Hz, 2H).

$^{13}$C NMR (101 MHz, CDCl$_3$) δ 165.61, 155.62, 148.89, 147.88, 145.54, 141.95, 141.57, 140.97, 139.12, 131.45, 131.36, 130.82, 130.56, 129.15, 128.97, 128.79, 128.72, 128.54, 128.51, 128.16, 127.09, 126.96, 126.91, 124.14, 122.92, 122.53, 121.42, 120.08, 115.24, 113.94.

4. Film Preparation and Photoluminescence Characterization

Representative film preparation: In a nitrogen-purged glove box, Example 1, Structure (ii) (10.2 mg) is added to a 20 mL screw-cap vial equipped with a magnetic stir bar. A dichloromethane solution containing 25 wt % polymethylmethacrylate (PMMA) (1 mL) is added. The vial is capped and the mixture/solution is stirred overnight. One or two drops of mixture/solution are filtered through a PTFE filter (0.2 mm) onto a glass microscope cover slip and allowed to dry overnight. The film is further dried in a vacuum oven at 60° C. for 48 hours. The oven is then cooled to room temperature and the film is promptly placed into a glovebox until emission characterization.

Emission spectra and quantum yields are collected on a PTI fluorimeter. Quantum yields are measured on PMMA doped films and obtained using an integrating sphere coupled to the spectrometer according to the following reference:

De Mello, J. C.; Wittman, H. F.; Friend, R. H. *Adv. Mater.* 1997, 9, 230-232.

Luminescence is collected using an excitation wavelength of 355 nm. The film is measured three times in which between each measurement, the film is removed, repositioned, and replaced.

Steady-state or time resolved emission profiles are collected at room temperature or 77 K on polymer films inside the sample chamber of the PTI fluorimeter using an excitation wavelength centered at 355 nm. The films are contained in standard borosilicate NMR tubes that are placed into quartz tipped EPR dewars. Low temperature spectra are acquired after filling the dewar with liquid nitrogen. The time-resolved emission spectra reported herein are acquired on the same samples utilizing the pulsed capabilities of the PTI fluorimeter.

The experimental estimate for the S1-T1 gap is obtained by collecting time-resolved emission spectra for doped PMMA films of the inventive composition. Triplet energy level (T1) is defined as the energy difference between the ground state singlet and lowest energy triplet excited state. This value is experimentally estimated by the x-axis intersection point of a tangent line drawn on the high energy side of the delayed component of the emission spectrum taken at 77 Kelvin (K). The singlet energy level (S1) is defined by the energy difference between the ground state singlet energy and the lowest energy singlet excited state. This value is experimentally estimated by the x-axis intersection point of a tangent line drawn on the high energy side of the prompt portion of the emission spectrum at 77 K. The S1-T1 gap is obtained by subtracting the S1 and T1 values.

FIG. 1 shows the photoluminescence spectra of Example 1, Structure (ii) in PMMA collected at room temperature and 77 K. At room temperature, Example 1 displays an emission maximum at 475 nm with a quantum yield of ~61% (see Table 2 for details).

FIG. 2 shows the photoluminescence spectra of Example 1, Structure (ii) when dissolved in chloroform. The initial intensity of the luminescence (black solid line) increases as the solution is sparged with $N_2$, displacing any dissolved $O_2$ in the solution (dashed line). The intensity then decreases once the cuvette cap has been briefly removed (dash-dot line). Taken together, these data indicate that the excited-state of Example 1, Structure (ii) is sensitive to $O_2$.

FIG. 3 shows time-resolved emission spectra (TRES) for Example 1, Structure (ii) in PMMA at 77 K. The higher energy prompt singlet emission component is observed in the earlier (in-pulse) delays. At longer delay times, the triplet emission is observed at lower energy. Based on this analysis, an energy separation of ~0.08 eV between the two excited states is estimated.

Details summarizing the photophysical characterization of Examples 1-4 are shown in Table 2. These data indicate that high quantum efficiencies can be obtained from films doped with a composition composed of Compound 1 and/or Compound 2. Also, the small experimental estimates for the S1-T1 gap are in good agreement with the computed values and support that these compositions can undergo thermally activated delayed fluorescence.

TABLE 2

Photoluminescence Characterization of Examples 1-4 in PMMA.

| Example | Room Temperature Emission Maximum | Room Temperature Quantum Yield | Estimated S1-T1 |
|---|---|---|---|
| Example 1. Structure (ii) | 475 nm | 61 ± 1% | 0.08 eV |
| Example 2. Structure (ix) | 488 nm | 16 ± 5% | 0.01 eV |
| Example 3. Structure (x) | 467 nm | 40 ± 5% | 0.03 eV |
| Example 4. Structure (xv) | 420 nm | 25 ± 5% | 0.34 eV |

Electroluminescent Device

An electroluminescent device is constructed using the following HTL, dopant/host (10 wt % dopant), and ETL layers, as shown in Table 3, in between standard anodes (ITO) and cathodes (Al). The HOMO-LUMO Gap is defined as the difference between the HOMO and LUMO values.

TABLE 3

Electroluminescent Device with calculated energies in eV.

| Material | HTL TPD | Dopant Structure (ii) | Host DPEPO | ETL AlQ3 |
|---|---|---|---|---|
| LUMO | −0.78 | −1.84 | −1.00 | −1.73 |
| HOMO-LUMO Gap | −3.89 | −3.04 | −5.33 | −3.27 |
| HOMO | −4.67 | −4.88 | −6.33 | −5 |
| Triplet | 3.1 | 3.0 | 3.44 | 2.88 |

The structures for TPD, Alq3, and DPEPO are provided below.

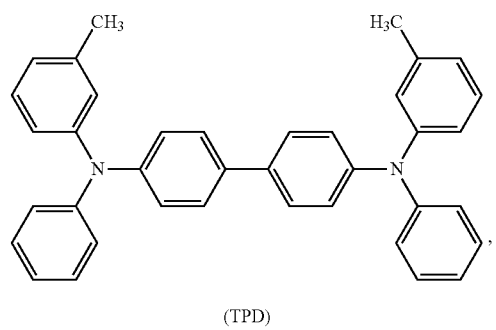

(TPD)

-continued

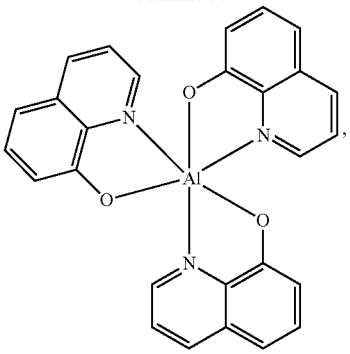

(Alq3)

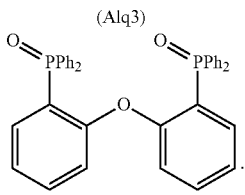

(DPEPO)

It is specifically intended that the present disclosure not be limited to the embodiments and illustrations contained herein, but include modified forms of those embodiments including portions of the embodiments and combinations of elements of different embodiments as come within the scope of the following claims.

The invention claimed is:

1. A composition comprising at least one compound selected from the group consisting of Compound 1, Compound 2, and combinations thereof, as shown below:

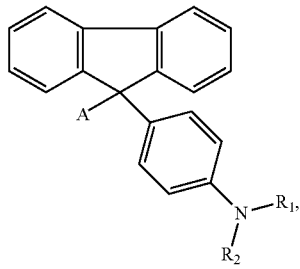
(Compound 1)

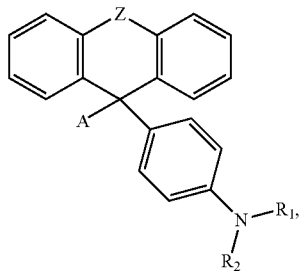
(Compound 2)

wherein, for Compound 1 and Compound 2, independently, $R_1$ and $R_2$ each independently is selected from the group consisting of hydrogen, a substituted alkyl, an unsubstituted alkyl, a substituted heteroalkyl, an unsubstituted heteroalkyl, a substituted aryl, an unsubstituted aryl, a substituted heteroaryl, and an unsubstituted heteroaryl;

wherein, for Compound 1 and Compound 2, independently, the Component A is Group a):

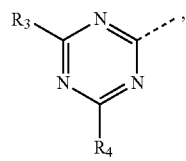
Group a)

wherein for Group a), $R_3$ and $R_4$ each independently is selected from the group consisting of hydrogen, a substituted alkyl, an unsubstituted alkyl, a substituted aryl, an unsubstituted aryl, a substituted heteroaryl, and an unsubstituted heteroaryl; and wherein, for Compound 2, Component Z is selected from the group consisting of $C(R_Z)_2$, $NR_Z$, $P(O)R_Z$, $PR_Z$, S, SO, $SO_2$, $Si(R_Z)_2$, and O;

wherein each $R_Z$, independently, is selected from the group consisting of hydrogen, an unsubstituted alkyl, an unsubstituted aryl, and an alkoxy; and wherein, optionally, for Compound 1 and Compound 2, independently, one or more hydrogen atoms may be substituted with deuterium.

2. The composition of claim 1, wherein the composition comprises Compound 1, and $R_1$ and $R_2$ for Compound 1 each independently is selected from the group consisting of a substituted aryl, an unsubstituted aryl, a substituted heteroaryl, and an unsubstituted heteroaryl.

3. The composition of claim 2, wherein the composition comprises Compound 1, and $R_1$ and $R_2$ for Compound 1 each independently is selected from the group consisting of an unsubstituted aryl and an unsubstituted heteroaryl.

4. The composition of claim 3, wherein the composition comprises Compound 1, and wherein for Group a), $R_3$ and $R_4$ each independently is selected from the group consisting of hydrogen, an unsubstituted aryl, and an unsubstituted heteroaryl.

5. The composition of claim 4, wherein the composition comprises Compound 1, and Compound 1 has the Structure (i):

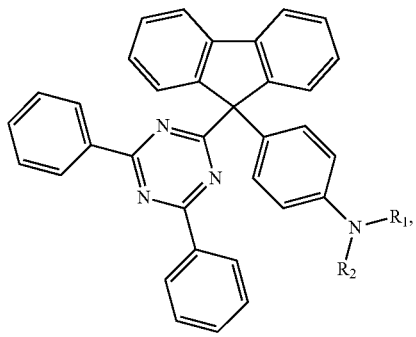
Structure (i)

wherein $R_1$ and $R_2$ for Structure (i) each independently is selected from the group consisting of an unsubstituted aryl and an unsubstituted heteroaryl.

6. The composition of claim 3, wherein the composition comprises Compound 1 wherein for Group a), $R_3$ and $R_4$ each independently is selected from hydrogen, an unsubstituted aryl, and an unsubstituted heteroaryl.

7. The composition of claim 6, wherein the composition comprises Compound 1, and Compound 1 has the Structure (i):

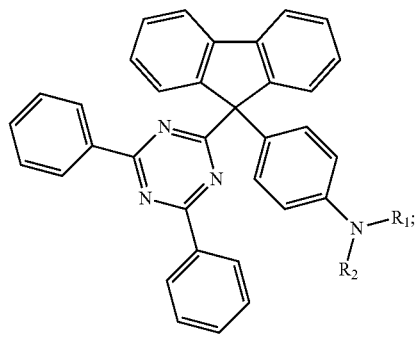

Structure (i)

and wherein for Structure (i), $R_1$ and $R_2$ each independently is selected from the group consisting of an unsubstituted aryl and an unsubstituted heteroaryl.

8. The composition of claim 3, wherein the composition comprises Compound 1, and Compound 1 has a structure selected from the group consisting of Structures (ii), (iii), (iv), (v) shown below

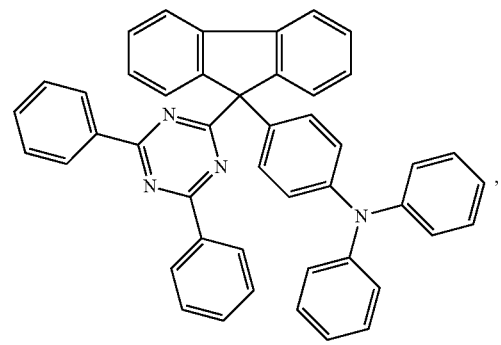

Structure (ii)

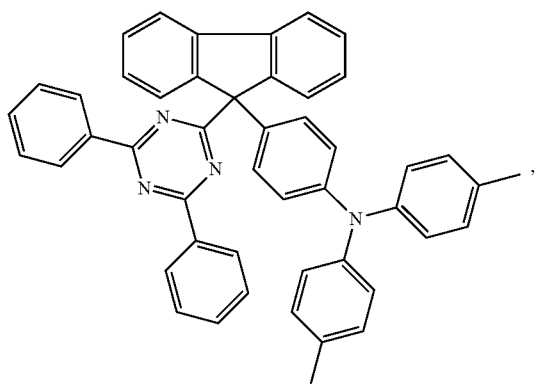

Structure (iii)

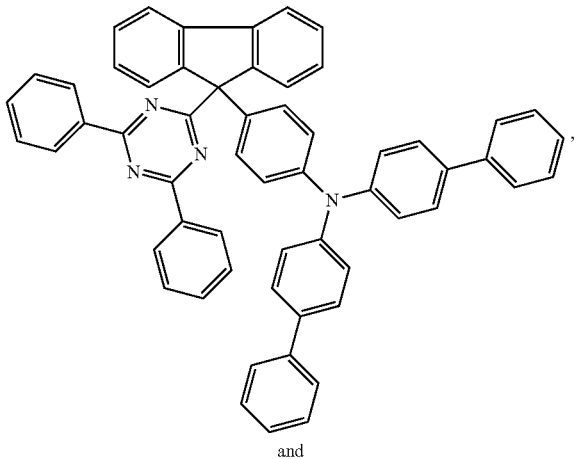

Structure (iv)

and

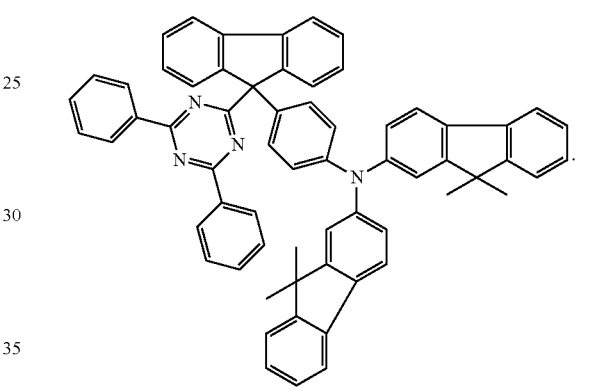

Structure (v)

9. The composition of claim 1, wherein the composition comprises Compound 2, and wherein for Compound 2, $R_1$ and $R_2$ each independently is selected from the group consisting of a substituted aryl, unsubstituted aryl, a substituted heteroaryl, and an unsubstituted heteroaryl.

10. The composition of claim 9, wherein the composition comprises Compound 2, and wherein for Group a), $R_3$ and $R_4$ each independently is selected from the group consisting of hydrogen, an unsubstituted aryl, or an unsubstituted heteroaryl.

11. The composition of claim 10, wherein the composition comprises Compound 2 having the Structure (viii)

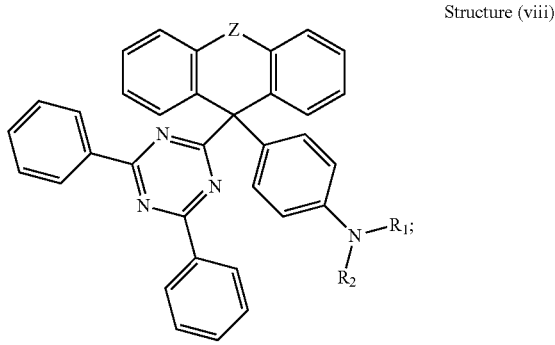

Structure (viii)

and wherein for Structure (viii), $R_1$ and $R_2$ each independently is selected from the group consisting of an unsubstituted aryl and an unsubstituted heteroaryl; and wherein, for Structure (viii), Component Z is selected from the group consisting of $CR_{(Z)2}$, $NR_Z$, $P(O)R_Z$, $PR_Z$, S, SO, $SO_2$, $SiR_{(Z)2}$, and O, and wherein Rz is selected from the group consisting of hydrogen, an unsubstituted alkyl, an unsubstituted aryl, and an alkoxy.

12. The composition of claim 9, wherein the composition comprises Compound 2
wherein for Group a), $R_3$ and $R_4$ each independently is selected from hydrogen, an unsubstituted aryl, and an unsubstituted heteroaryl.

13. The composition of claim 12, wherein the composition comprises Compound 2, and Compound 2 has the Structure (viii):

Structure (viii)

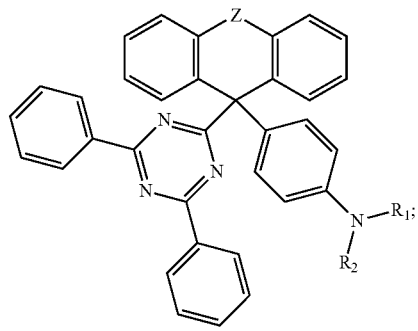

and
wherein for Structure (viii), $R_1$ and $R_2$ each independently is selected from the group consisting of a substituted aryl, an unsubstituted aryl, a substituted heteroaryl, and an unsubstituted heteroaryl;
wherein for Structure (viii), Component Z is selected from the group consisting of $CR_{(z)2}$, $NR_z$, $P(O)R_z$, $PR_z$, S, SO, $SO_2$, $SiR_{(z)2}$, and O; and
wherein $R_z$ is selected from the group consisting of hydrogen, unsubstituted, alkyl, unsubstituted aryl, and an alkoxy.

14. The composition of claim 9, wherein the composition comprises Compound 2 and Compound 2 has a structure selected from the group consisting of Structure (ix), (x), (xi), (xii), and (xiii), provided below Structure (ix)

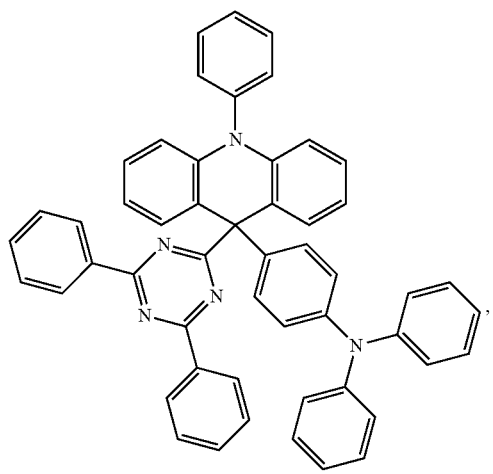

Structure (x)

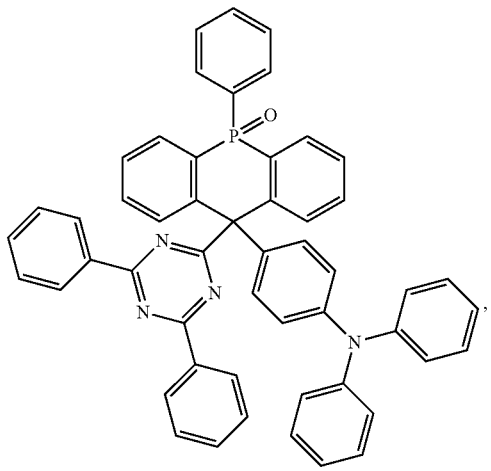

Structure (xi)

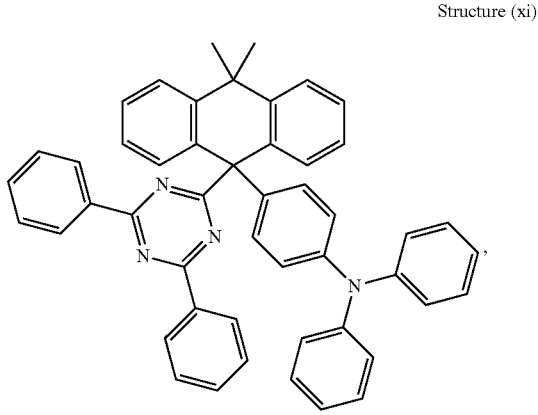

Structure (xii)

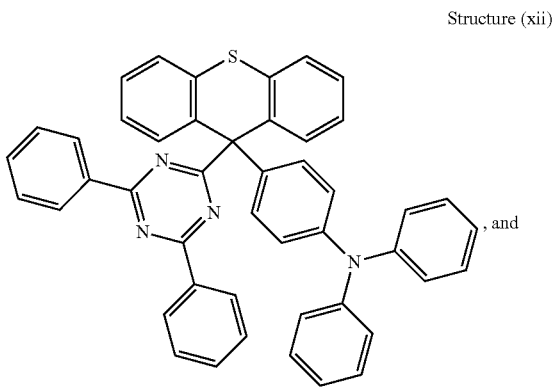

, and

-continued
Structure (xiii)
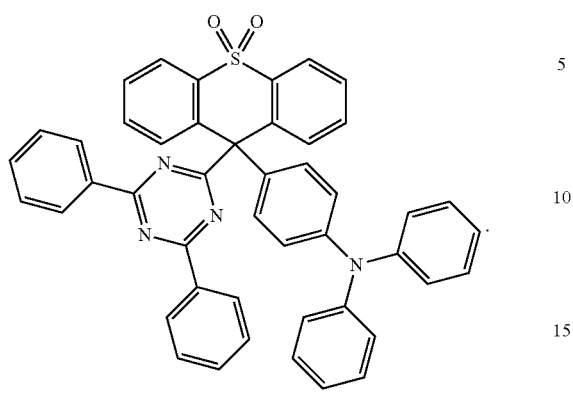
15. An electronic device comprising at least one component formed the composition of claim 14.
* * * * *